United States Patent [19]

Suwaki et al.

[11] 4,375,818
[45] Mar. 8, 1983

[54] ULTRASONIC DIAGNOSIS SYSTEM ASSEMBLED INTO ENDOSCOPE

[75] Inventors: Toshitaka Suwaki, Hachioji; Otaro Ando, Hino, both of Japan

[73] Assignee: Olympus Optical Company Ltd., Japan

[21] Appl. No.: 121,031

[22] Filed: Feb. 13, 1980

[30] Foreign Application Priority Data

| Mar. 12, 1979 | [JP] | Japan | 54-28488 |
| Mar. 16, 1979 | [JP] | Japan | 54-31323 |
| Mar. 16, 1979 | [JP] | Japan | 54-31324 |
| Mar. 27, 1979 | [JP] | Japan | 54-35019 |
| May 9, 1979 | [JP] | Japan | 54-56464 |
| May 9, 1979 | [JP] | Japan | 54-56465 |
| May 28, 1979 | [JP] | Japan | 54-64920 |
| Jul. 19, 1979 | [JP] | Japan | 54-90904 |

[51] Int. Cl.³ .............................. A61B 10/00
[52] U.S. Cl. .............................. 128/660; 128/4
[58] Field of Search ........... 128/660-663, 128/4-8

[56] References Cited

U.S. PATENT DOCUMENTS

| 3,779,234 | 12/1973 | Eggleton et al. | 128/660 |
| 3,888,237 | 6/1975 | Mori | 128/6 X |
| 3,927,661 | 12/1975 | Takemura | 128/660 |
| 3,938,502 | 2/1976 | Bom | 128/661 X |
| 4,034,744 | 7/1977 | Goldberg |  |
| 4,047,520 | 9/1977 | Soldner et al. |  |
| 4,101,795 | 7/1978 | Fukumoto et al. | 128/660 X |
| 4,217,516 | 8/1980 | Iinuma et al. | 128/660 X |
| 4,273,111 | 6/1981 | Tsukoya | 128/660 X |

OTHER PUBLICATIONS

Ikukoshi, Y., "Apparatus for Eudoscopic and UTS Medical Diagnosis", Jap. Publ. Unexam. Pat. Appln. P. Sho-54/1984, Jan. 9, 1979.
Hisanaga, K., et al., "A New Transesophogeal Real Time Linear Scanner and Initial Clinical Results", Proc. 23rd AIUM, 1978, p. 112.
Hisanaga, K., et al., "A New Trans-digestive Tract Scanner With a Gastro-Fiber Scope", Proc. 23rd AIUM P. 1705, 1978.
Taylor, W. B. et al., "A High Resolution Transrectal UTS System", UTS in Meds. Biol., pp. 129-138, vol. 5, 1979.

*Primary Examiner*—Kyle L. Howell
*Assistant Examiner*—Francis J. Jaworski
*Attorney, Agent, or Firm*—Ostrolenk, Faber, Gerb & Soffen

[57] ABSTRACT

An ultrasonic diagnosis system includes an ultrasonic wave transmitting and receiving transducer which is rockably disposed within the distal end of a portion of an endoscope which is adapted to be inserted into a coeliac cavity. The transducer emits ultrasonic wave from within the coeliac cavity and directs it toward internal tissues of a physical body, thereby enabling an ultrasonic tomographic image to be obtained. The endoscope also includes an observation optical system which permits the location of the ultrasonic transducer within the coeliac cavity to be visually recognized.

42 Claims, 40 Drawing Figures

F I G. 12
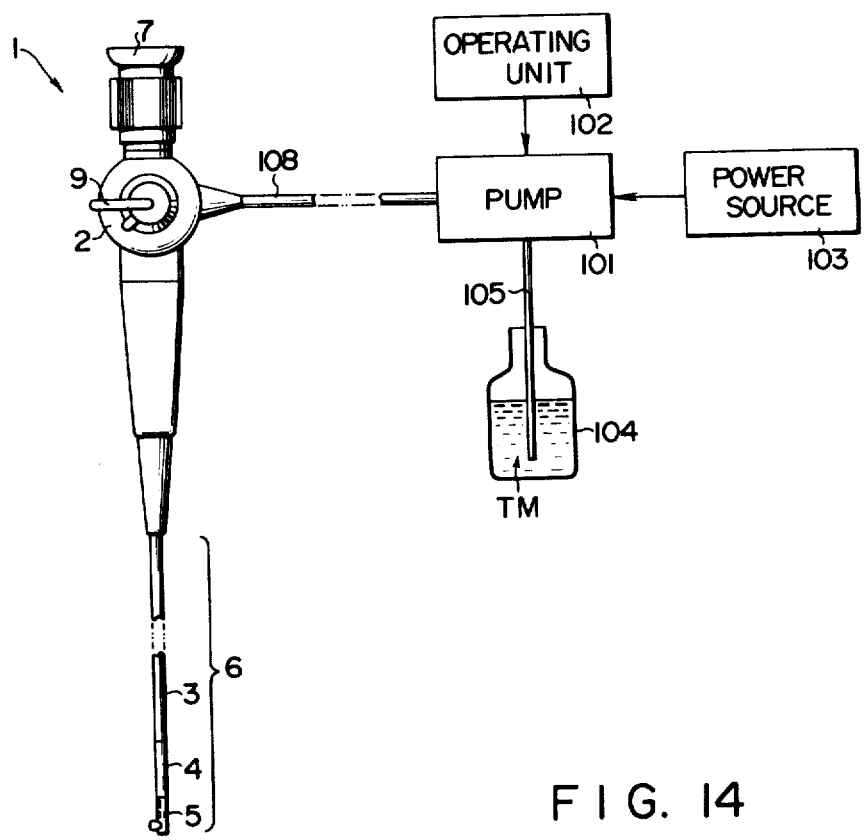
F I G. 14
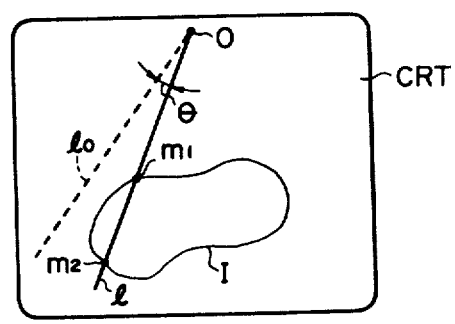

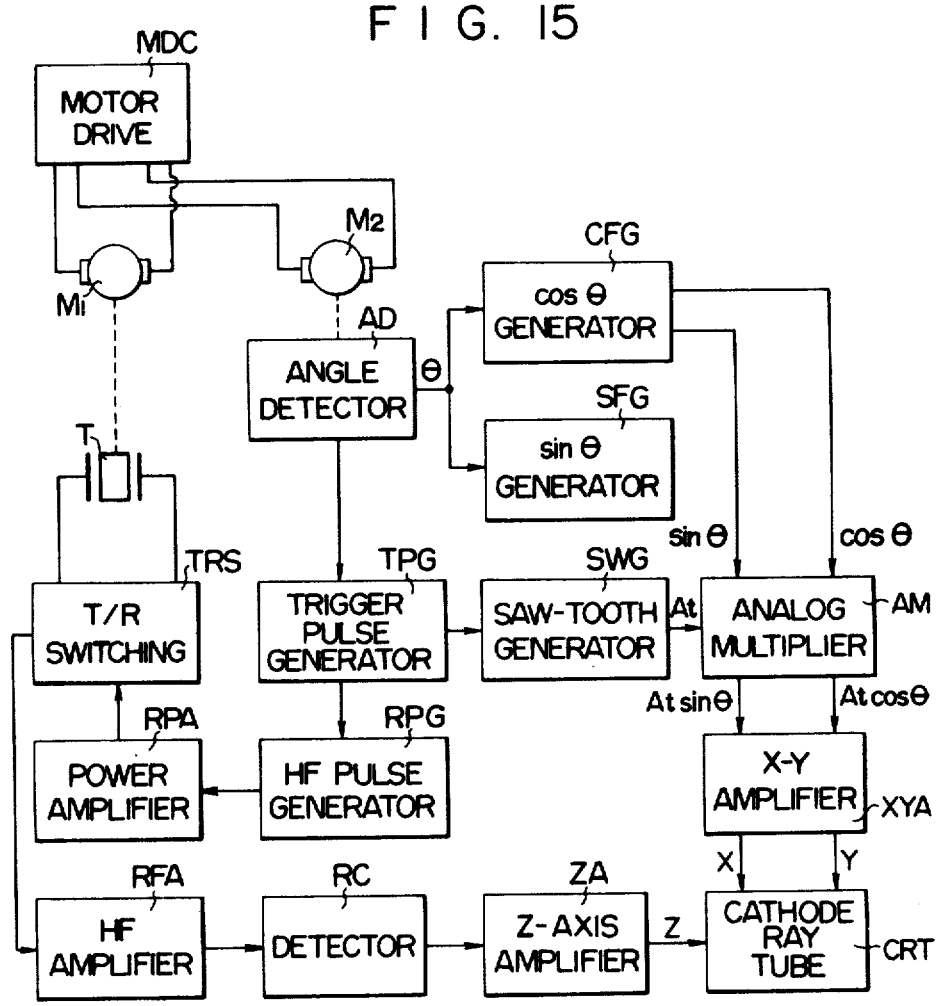
F I G. 15

FIG. 19
FIG. 21
FIG. 22
FIG. 20
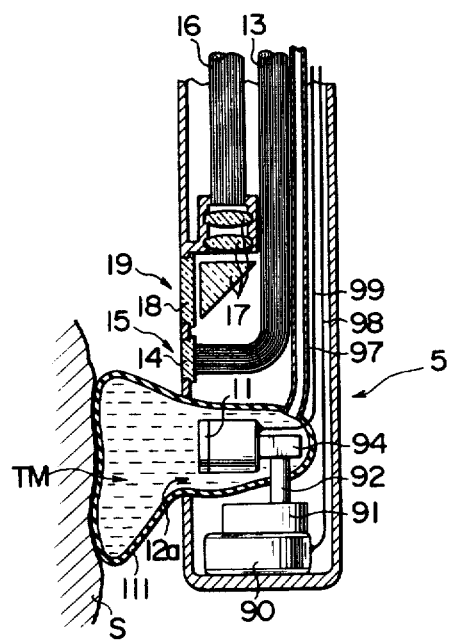
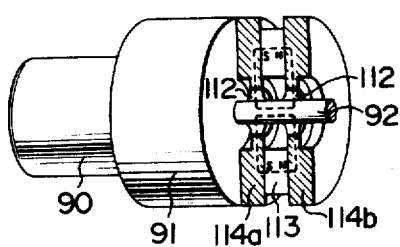
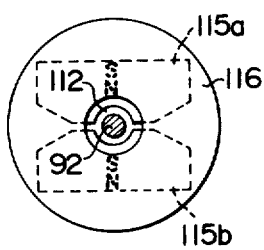
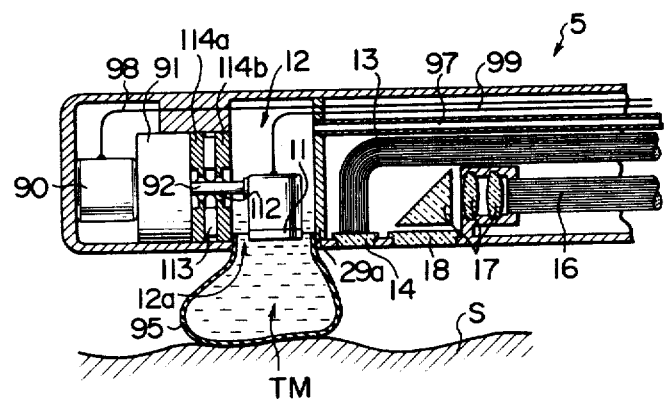

F I G. 34
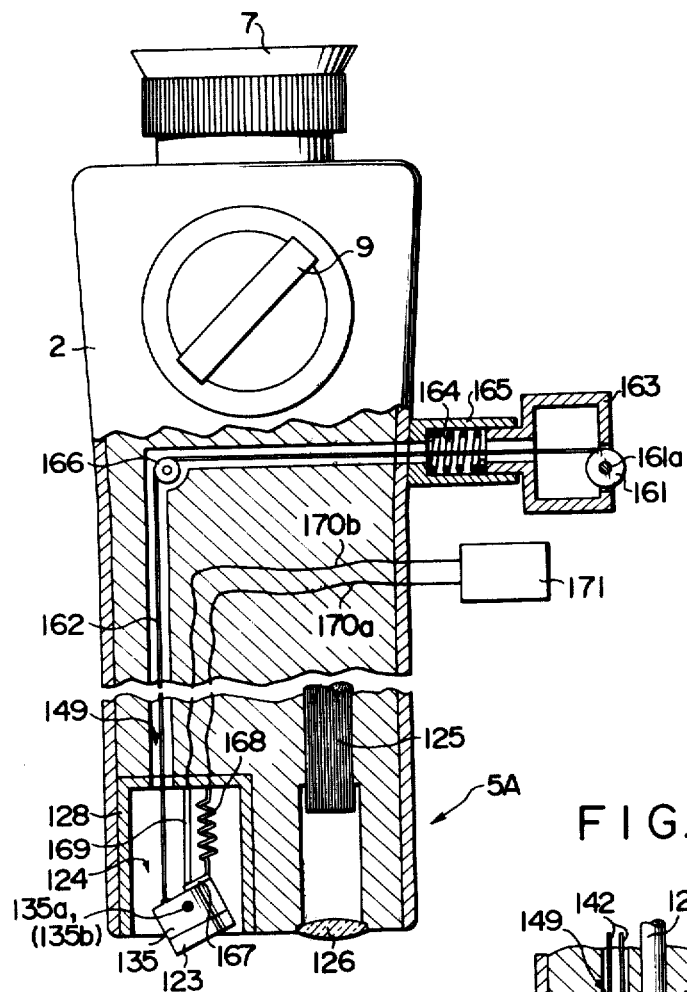
F I G. 35
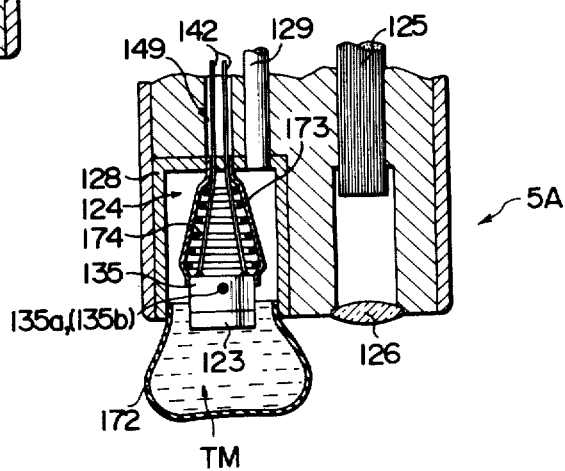

ULTRASONIC DIAGNOSIS SYSTEM ASSEMBLED INTO ENDOSCOPE

BACKGROUND OF THE INVENTION

The invention relates to an ultrasonic diagnosis system assembled into an endoscope, and more particularly, to such system which includes an ultrasonic wave transmitting and receiving transducer rockably mounted within the distal end of a portion of an endoscope which is adapted to be inserted into a coeliac cavity to effect a B-mode sector scan thereof to produce a reconstructed image of internal tissues.

As is recognized, the recent advance in the ultrasonic imaging art has established an ultrasonic diagnosis technique which is extensively useful for diagnostic purposes by forming an echo image by means of an ultrasonic scanning of an affected part of a physical body. The technique comprises transmitting an ultrasonic wave into the physical body of a patient from the surface thereof, receiving a reflected wave or echo from the interior, and forming an ultrasonic tomographic image of various organs within the body on the basis of acoustical information contained in the reflected wave, thus enabling the image to be utilized for purpose of diagnosis.

The described ultrasonic imaging technique has a number of advantages over the radiography which has been conventionally used in the medical art in that an image of soft tissues of a living body can be easily produced without the use of contrast medium, that the technique is free from the likelihood of causing adverse influences of radioactivity and is harmless to a living body, that it lends itself to locate calculus or cancer tissues, and that the equipment required is inexpensive and easy to operate. The technique has rapidly increasing applications inasmuch as the quality of the image formed is greatly improved as a result of the recent advance in the art.

However, with the conventional ultrasonic diagnosis system, in almost every instance, the ultrasonic wave is transmitted from and received on the surface of the physical body of a patient in order to produce an image of various organs located within the body. Hence, the distance to the organ being scanned is usually large enough to prevent a sharp image of high resolution from being produced. Moreover, the passage of the ultrasonic wave through a non-uniform layer such as subcutaneous fat results in a reduction in the S/N ratio of the echo signal. Alternatively, the presence of a gaseous layer such as a coeliac cavity or air-bladder in the path of the ultrasonic wave causes the ultrasonic energy to be absorbed and attenuated, even leading to a difficulty in the imaging process. In addition, when the organ is located behind a bone, the imaging is disabled by the attenuation of the ultrasonic wave which is either reflected or absorbed by the bone.

To overcome these drawbacks or difficulties experienced in the ultrasonic imaging process when the wave is transmitted from the surface of the physical body, it has been proposed to transmit an ultrasonic wave from within a coeliac cavity in producing an image of internal organs. As compared with ultrasonic imaging from the outer surface of the physical body, the ultrasonic imaging from within a coeliac cavity offers a number of major advantages:

(1) in that a diagnosis from a location more closely spaced from an organ of a living body is made possible, permitting the use of an ultrasonic wave of higher frequency with improved resolution;

(2) a diagnosis of those organs which have been heretofore difficult or impossible to image from the outer surface due to the presence of coeliac cavity, air-bladder or bone is made possible; and (3) the process is not subject to the influence of subcutaneous fat which varies from patient to patient, enabling a more accurate diagnosis. Several types of apparatus have already been proposed which are directed to the ultrasonic imaging from within a coeliac cavity. By way of example, an ultrasonic diagnostic apparatus is known in which an ultrasonic transducer is placed into the rectum and rotated within a pouch containing water to effect a radar scan for examining the prostate gland. Also known is an arrangement including a transducer which is mounted in the distal end of a catheter for insertion into the main artery or the heart, or an arrangement including an ultrasonic transducer which is mounted on the tubular side of a sonde which is mounted for axial displacement for scanning purpose. Finally, an arrangement is also known in which a plurality of ultrasonic transducers are disposed in an array on the tubular side of a sonde along the axial direction or the circumferential direction and are electrically switched in a sequential manner to provide a linear scan.

However, these ultrasonic diagnosis systems are not provided with means which permits an optical observation of the interior of a coeliac cavity, so that when any one of these systems is inserted into the coeliac cavity, there remains a disadvantage that the location where the ultrasonic transducer is disposed within the cavity or in which direction it is oriented cannot be known. Also, when the system is being inserted into the coeliac cavity, the inability to observe the interior of the coeliac cavity creates a risk. While the placement of the system into a relatively shallow coeliac cavity having a simple configuration such as the rectum or the gullet may be possible, it is very difficult to place it into a coeliac cavity which is complex in configuration and has a substantial depth such as the stomach, the duodenum or the colon, requiring a very high level of skill. Hence, it is obvious that there is a need for an ultrasonic diagnosis system capable of an ultrasonic imaging and which permits an optical observation of the interior of a coeliac cavity.

On the other hand, an endoscope is popularly utilized to provide an optical observation of the interior of a coeliac cavity. Hence, it would appear that an ultrasonic diagnosis system which eliminates the described disadvantages can be obtained by assembling an ultrasonic transducer into the distal end of an endoscope which is provided with an optical observation unit which permits an observation of a coeliac cavity. However, the implementation of such an ultrasonic diagnosis system involves the following two technical problems:

(1) A medical endoscope which can be inserted into a coeliac cavity without undue pain or damage to a patient must be limited in its thickness. By way of example, the limit on the diameter of an endoscope which is passed through the gullet to observe the stomach or the duodenum is on the order of 13-14 mm. Accordingly, an ultrasonic transducer of a reduced size must be used in order to incorporate it into the endoscope. However, a currently available ultrasonic transducer assembly which is used to provide an electronic sector scan and including a plurality of elements has dimensions on the order of 10×13×16 mm, and hence cannot be received within the endoscope. Thus, only a single element, ultrasonic transducer can be used.

(2) When a single element, ultrasonic transducer is employed to produce a two-dimensional tomographic image, some mechanical scan technique must be used. To this end, a drive mechanism must be incorporated into the endoscope.

In consideration of these factors, it will be seen that a B-mode mechanical sector scan technique using a single element, ultrasonic transducer will be an optimum solution to the incorporation of an ultrasonic diagnosis system into an endoscope while overcoming the problems mentioned under (1) and (2) above. The B-mode mechanical sector scan technique permits an imaging over an extensive area of a living body with a limited rocking motion of the ultrasonic transducer, and thus is optimally adapted to be used in an arrangement such as an endoscope which affords a limited space.

SUMMARY OF THE INVENTION

It is an object of the invention to provide an ultrasonic diagnosis system assembled into an endoscope in which an ultrasonic wave transmitting and receiving transducer is rockably disposed in a housing which is located in the distal end of a portion of an endoscope adapted to be inserted into a coeliac cavity, adjacent to an illumination window and an observation window formed therein and wherein the transducer is associated with a transducer drive means and a scan angle detector means so that the combination of a transducer output and the scan angle enables a B-mode sector scan image of an affected part to be formed.

It is another object of the invention to provide an ultrasonic diagnosis system of the type described in which the housing has an opening which is closed by an enclosure and in which there is provided means for supplying or displacing an ultrasonic wave transmitting medium so that during an ultrasonic imaging operation, ultrasonic energy is transmitted between an organ within the physical body and the ultrasonic transducer through the transmitting medium which fills the enclosure.

It is a further object of the invention to provide an ultrasonic diagnosis system of the type described in which the ultrasonic transducer has an ultrasonic damper layer which is integrally provided with support means which rockably supports the transducer in a manner such that the transducer can be received within the housing in a compact manner.

It is still another object of the invention to provide an ultrasonic diagnosis system of the type described in which the ultrasonic transducer is driven for rocking motion by a drive motor which is disposed in the distal end of the endoscope in a manner to be neatly disposed within the endoscope.

It is a still further object of the invention to provide an ultrasonic diagnosis system of the type described in which the ultrasonic transducer can be rocked by an operator disposed at the proximate end of the endoscope and connected therewith through a drive wire, thereby enabling the system to be assembled into the endoscope without increasing the size of the distal end of the endoscope.

It is an additional object of the invention to provide an ultrasonic diagnosis system of the type described in which the drive means includes a pulse motor which is used as a drive motor and wherein drive pulses supplied thereto are counted to derive information indicating a scan angle of the transducer.

It is yet another object of the invention to provide an ultrasonic diagnosis system of the type described in which in addition to the drive motor which comprises the drive means associated with the ultrasonic transducer, there is provided another detection motor which is fed from the common power source or a separate power source synchronized therewith and in which a scan angle of the transducer is derived from an angle of rotation of the detection motor.

It is still an additional object of the invention to provide an ultrasonic diagnosis system of the type described and additionally including a magnetic circuit located in a wall defining a boundary between the housing of the ultrasonic transducer and a housing for the drive motor and which is filled with a magnetic fluid so that the drive motor is sealed from the ultrasonic wave transmitting medium received within the housing by means of the magnetic fluid.

In accordance with the invention, an ultrasonic transducer can be inserted deeply into a coeliac cavity together with the distal end of an endoscope, so that the distance from the transducer to an organ of a living body, an ultrasonic tomographic image of which is to be formed, can be reduced, permitting ultrasonic energy to be emitted from a closely spaced location. This reduces the influence of adjacent tissues of the living body as by absorption of ultrasonic energy. Hence, ultrasonic energy of a high frequency on the order of 5–10 MHz can be used. The reduced wavelength of the ultrasonic wave significantly improves the resolution of a reconstructed image as compared with the prior art devices.

Since the ultrasonic energy is transmitted and received within a coeliac cavity, there is no passage through the subcutaneous fat layer or through those portion of the living body such as bones which give rise to interference, thus assuring that a desired organ can be imaged by passing through relatively uniform tissues of the body to improve the S/N ratio of the ultrasonic tomographic image.

An organ such as the pancreas, which is anatomically located at a position which prevents satisfactory ultrasonic imaging from the surface of the body, can be easily imaged through the wall of the stomach or the like.

The use of the ultrasonic diagnosis system in combination with an observation optical system of the endoscope enables both an optical image of the inner wall of the coeliac cavity and the ultrasonic tomographic image of tissues located behind the wall to be simultaneously observed for purpose of diagnosis. This also permits the ultrasonic energy to be exactly directed toward a location which is determined by an observation through the observation optical system.

Since the ultrasonic energy is transmitted to or received from tissues of the living body through the ultrasonic wave transmitting medium which fills the enclosure, the attenuation of the ultrasonic energy by gaseous substances present within the coeliac cavity can be minimized, thus improving the S/N ratio of the tomographic image.

A pivoting mechanism which rockably supports the ultrasonic transducer is provided in integral relationship therewith to provide an increased surface area from which the ultrasonic energy is emitted while utilizing the limited space within the endoscope to the maximum extent. This improves a directivity response of the ultrasonic beam, contributing to the improvement of the resolution of the tomographic image.

The ultrasonic transducer may be rocked for scanning purposes, by a drive motor which is disposed in the distal end of the endoscope. In this manner, means required to transmit a drive to the transducer is simplified, enabling the entire mechanical scanning assembly of the system to be reduced in size and weight.

In addition, the ultrasonic transducer may be rocked for scanning purposes by means of a drive motor which is disposed at the proximate end of the endoscope. In this manner, the distal end of the endoscope in which the mechanical scanning assembly of the system is disposed can be reduced in size and weight.

The drive motor which is used to rock the ultrasonic transducer for scanning purpose comprises a pulse motor, and drive pulses applied to the pulse motor are counted to derive information which indicates a scan angle of the ultrasonic transducer, thus dispensing with a separate scan angle detector means and simplifying the mechanical scanning assembly of the system.

A scan angle detecting motor may be provided separately from the drive motor so as to operate in synchronized relationship with the latter. The detecting motor can be connected to a scan angle detection means, whereby the distal end of the endoscope in which the mechanical scanning assembly of the system is disposed can be reduced in size and weight.

A magnetic circuit filled with a magnetic fluid may be disposed in a wall which defines a boundary between the transducer housing and the drive motor housing to minimize a mechanical loss of the output from the drive motor and to provide a water tight seal for the housing.

BRIEF DESCRIPTION OF THE DRAWINGS

FIG. 12 is a block diagram illustrating means for supplying and displacing an ultrasonic wave transmitting medium to or from the mechanical scanning assembly in the system of FIG. 11;

FIG. 14 illustrates the screen of a cathode ray tube, depicting an ultrasonic tomographic image reconstructed with the system shown in FIG. 13;

FIGS. 15 to 18 are block diagrams of alternative electrical circuits which may be used for an imaging apparatus of the ultrasonic diagnosis system of the invention;

FIG. 19 is a cross section of a modified enclosure which may be used in the system shown in FIG. 11;

FIG. 20 is a cross section of another form of the mechanical scanning assembly of the system shown in FIG. 11;

FIG. 21 is a perspective view, partly in section, showing the detail of the magnetic circuit in the system shown in FIG. 20;

FIG. 22 is a front view illustrating another form of the magnetic circuit;

FIG. 34 is a cross section showing a further form of drive means for the ultrasonic transducer;

FIG. 35 is a cross section of a modified form of the ultrasonic diagnosis system shown in FIGS. 29 and 30 having an enclosure provided therewith;

DESCRIPTION OF PREFERRED EMBODIMENTS

Figure 1:
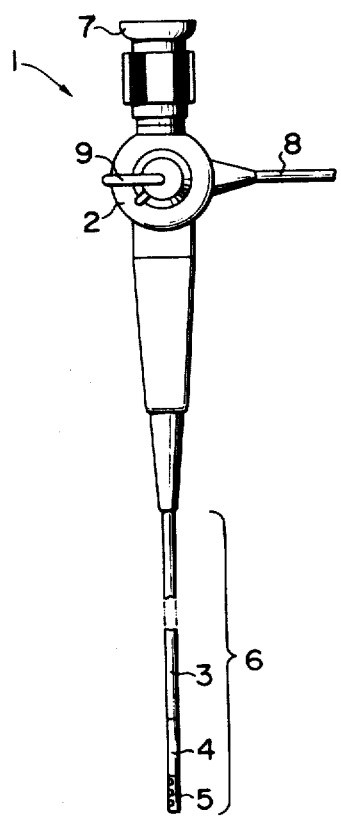
FIG. 1 is a plan view of an endoscope in which the ultrasonic diagnosis system of the invention can be assembled.

Referring to FIG. 1, there is shown one form of an endoscope in which the ultrasonic diagnosis system of the invention is assembled, in plan view. The endoscope 1 itself comprises a flexible endoscope of lateral view type which is well known in the art. Essentially, it comprises an operator 2 located at the proximate end of the endoscope and externally therefor for performing various operations, and an insertable portion 6 connected to the operator 2 and including a flexible portion 3 formed by a tubular body of a reduced diameter, a bending portion 4 and a distal end 5 connected to each other in a sequential manner. The flexible portion 3, bending portion 4 and distal end 5 define together the insertable portion 6 which can be inserted into a coeliac cavity of a patient. When inserting the endoscope, the distal end 5 is initially inserted into the coeliac cavity.

Figure 2:
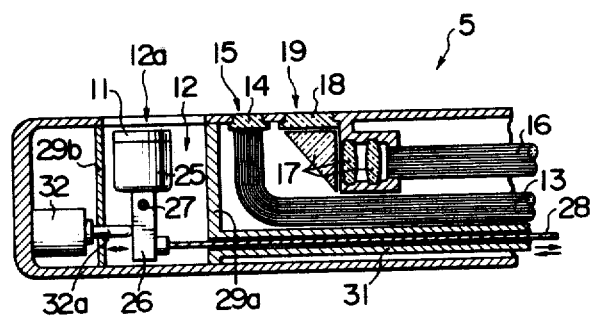
FIG. 2 is a longitudinal cross section of a mechanical scanning assembly of the ultrasonic diagnosis system according to one embodiment of the invention which is assembled into the distal end of the endoscope shown in FIG. 1.

As shown in FIG. 2, an opening 12a, an illumination window 15 and an observation window 19 are axially aligned and sequentially disposed along distal end 5. The window 15 is formed in a housing 12 in which an ultrasonic wave transmitting and receiving transducer (hereafter simply referred to as ultrasonic transducer) 11 used in the ultrasonic diagnosis system of the invention is disposed. The illumination 15 is defined by a cover glass 14 and is disposed in opposing relationship with one end face of a bundle of optical fibres 13 which serves as a light guide. The observation window 19 is defined by a cover glass 18 disposed in opposing relationship, through an imaging optical system 17, with one end face of a bundle of optical fibers 16 which serves as an image guide. The image guide or the bundle of optical fibres 16 extends through the bending portion 4 and the flexible portion 3 to the proximate end operator 2, with its other end face disposed in opposing relationship with an eyepiece assembly 7 mounted on the operator 2. The light guide or the bundle of optical fibres 13 also extends through the bending portion 4 and the flexible portion 3 to the proximate end operator 2, and is further connected through a connecting tube 8 with a source of illuminating light (not shown). Thus, by viewing the eyepiece assembly 7, the inner wall of a coeliac cavity which is illuminated by light from the source can be observed. It is to be noted that numeral 9 in FIG. 1 indicates a bending control lever which controls a bending of the bending portion 4.

Figure 3:
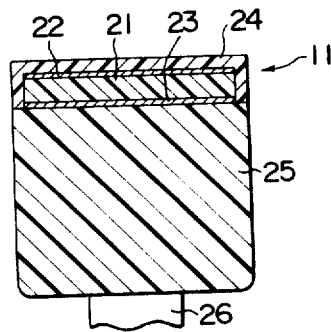
FIG. 3 is a cross section of an ultrasonic transducer which may be used in the system of FIG. 2.

As shown in FIG. 3, the ultrasonic transducer 11 comprises a vibrator 21, formed of an electrostrictive material such as PZT (lead zirconate titanate, Pb(Zr,Ti)O$_3$), lithium niobate (LiNbO$_3$) with a pair of electrode layers 22, 23 applied to the upper and the lower surface thereof. An insulating coat 24 of a material such as epoxy resin is applied to the upper surface of the electrode layer 22, which represents an ultrasonic energy emitting surface, as well as to the lateral sides of the transducer 11 in order to provide a matching of an acoustical impedance with an ultrasonic wave transmitting medium such as deaerated water, and to provide an electrical insulation. An ultrasonic damper layer 25 which comprises an ultrasonic energy absorbing material, as may be formed by powder of epoxy tungsten or tungstenate in admixture with an organic resin such as epoxy resin, is secured to the lower surface of the electrode layer 23. The ultrasonic damper layer 25 serves to absorb any ultrasonic energy which may be emitted from the lower surface of the electrode layer 23, located on the opposite side from the ultrasonic energy emitting surface of the transducer 11. As illustrated in FIG. 2, securely bonded to the lower surface of the ultrasonic damper layer 25 is the upper end of a support member 26 which is integrally fixed on a support pin or pivot 27 which is in turn rotatably mounted. A drive wire 28 has its one end secured to the lower end of the support member 26, and can be pulled and released to cause the support member 26 to oscillate about the pivot 27. Thus it will be seen that such oscillation of the support member 26 causes the ultrasonic transducer 11 to rock in an axial plane of the distal end 5, thus effecting a mechanical sector scan. The distal end of the drive wire 28 is passed through a flexible guide tube 31 which is fixedly connected with a partition wall 29a which defines the housing 12, and its other end extends to the proximate end operator 2 where it is connected to a drive unit (not shown) such as a motor so as to be selectively pulled and released.

A scan angle transducer or linear potentiometer 32 has an access shaft 32a which extends through a partition wall 29b, which also defines the housing 12, and bears against one lateral side or the left-hand side as viewed in FIG. 2, of the support member 26 to detect the scan angle of the ultrasonic transducer 11. The access shaft 32a is connected to a movable contact of the potentiometer 32, and is urged as by spring to project forward so that it assumes a position which uniquely corresponds to an angular position of the ultrasonic transducer 11. Consequently, the position of the access shaft 32a is detected by the potentiometer 32 as a potential difference, which represents a scan angle of the ultrasonic transducer 11.

Figure 4:
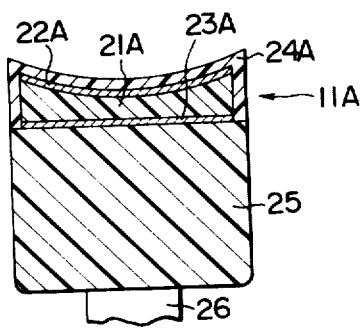
FIGS. 4 and 5 are cross sections showing alternative forms of the ultrasonic transducer.

FIG. 4 shows another form of the ultrasonic transducer in cross section. The ultrasonic transducer 11A of this Figure comprises an ultrasonic vibrator 21A having its upper surface which represents the ultrasonic energy emitting surface formed as a concave surface, and a pair of electrode layers 22A, 23A are applied to the both major surfaces of the vibrator. With this ultrasonic transducer 11A, the ultrasonic beam which is emitted by the emitting surface will converge to a focal point, and hence the ultrasonic beam will be sharply focused at a location within the physical body the diagnosis of which is desired, thus improving the azimuthal resolution of the tomographic image. It is to be noted that an insulating coat 24A is applied to the ultrasonic energy emitting surface of the transducer 11A.

Figure 5:
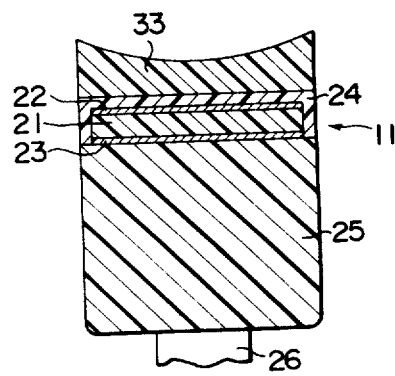

FIG. 5 shows a further form of the ultrasonic transducer in cross section. The ultrasonic transducer 11A itself is formed with a concave, ultrasonic energy emitting surface in order to achieve the convergence of the ultrasonic beam. However, in the form shown in FIG. 5, a similar effect is achieved by applying an acoustical lens 33 formed of epoxy resin, for example, and having its upper surface formed as a concave surface, to the ultrasonic energy emitting surface of the flat transducer as shown at 11 of FIG. 3, as by cementing.

Figure 6:
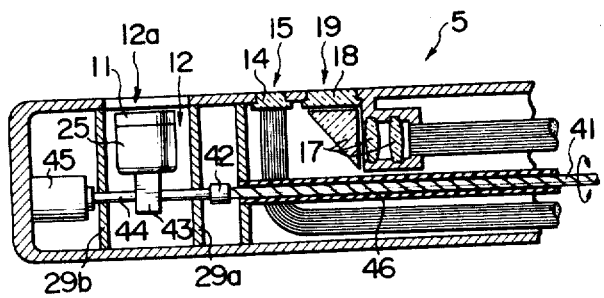
FIG. 6 is a longitudinal cross section of another form of mechanical scanning assembly which may be used in the system of FIG. 2.

FIG. 6 shows another form of drive means which drives the ultrasonic transducer 11. In contrast to the system shown in FIG. 2 where the drive wire 28 is used to drive the transducer 11, the drive means of FIG. 6 comprises a flexible rotatable shaft 41. The rotatable shaft 41 is formed of a material such as wire having a relatively small torsion, and is connected to one end of a support shaft 44 by means of a mounting member 42. The support shaft 44 is fixedly mounted in a support member 43 connected to the transducer 11, and is rotatably supported by partition walls 29a, 29b. The support shaft 44 is formed integrally with a rotating shaft of a rotary scan angle transduced potentiometer 45, which represents means for detecting a scan angle of the ultrasonic transducer 11. Thus an angle of rotation of the support shaft 44 is read by the potentiometer 45 as representing a scan angle of the transducer 11. The rotatable shaft 41 extends through a flexible guide tube 46 to the proximate end operator 2 where its other end is driven for rotation by drive means, not shown.

Other members and elements not referred to specifically are similar to the system shown in FIG. 2, and a repeated description thereof is omitted by using like reference characters for corresponding elements.

When the drive means for the ultrasonic transducer 11 is constructed in this manner, the ultrasonic energy emitting surface of the transducer 11 will be directed in a direction perpendicular to the axial direction of distal end 5 of the endoscope 1, and hence a scan of the transducer 11 takes place in the radial direction of the distal end 5.

Figure 7:
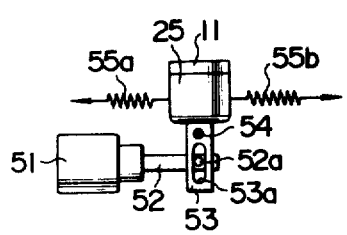
FIGS. 7 and 8 are schematic front views illustrating other forms of drive means associated with the ultrasonic transducer which is used in the mechanical scanning assembly of the system shown in FIGS. 2 and 6.
Figure 8:
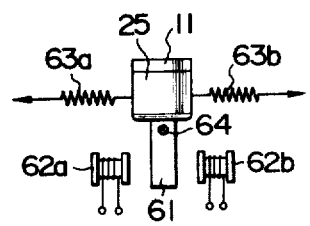

FIGS. 7 and 8 show other forms of drive means for the ultrasonic transducer 11. The drive means shown in FIG. 7 comprises a dynamoelectric voice coil actuator 51 having an output shaft 52 on which a pin 52a is fixedly mounted for cooperation with an elongate slot 53a formed in a support member 53 associated with an ultrasonic transducer 11. The transducer 11 is pivotally mounted on a pin 54. It will be noted that the transducer 11 is pulled in opposite directions by a pair of coiled tension springs 55a, 55b which are connected to the opposite sides of an ultrasonic damper layer 25, the other end of these coils being anchored to a stationary member so that the transducer normally remains still at a balanced position of the resilience of the both springs 55a, 55b. The drive means shown in FIG. 8 comprises a pair of electromagnets 62a, 62b disposed in opposing relationship with each other on the opposite sides of a support member 61 which is formed of a magnetically soft material. As in FIG. 7, an ultrasonic transducer 11 is pulled in opposite directions by a pair of coiled tension springs 63a, 63b. When either electromagnet 62a or 62b is fed with an exciting current, the support member 61 is attracted thereto, thereby making it possible for the transducer 11 to effect a scanning movement about a pivot 64 about which it is rotatable. A scan angle of the described transducers 11 can be detected from a drive current for the voice coil actuator 51 or an exciting current of the electromagnets 62a, 62b. However, it should be understood that a separate scan angle detecting potentiometer or other means may be provided.

Figure 9:
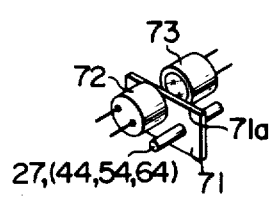
FIGS. 9 and 10 are perspective views of other forms of scan angle detection means disposed within the mechanical scanning assembly of the system shown in FIGS. 2 and 6.

FIG. 9 shows a further form of scan angle transducer or detection means associated with the ultrasonic transducer used in the ultrasonic diagnosis system of the invention. A light shield plate 71 is integrally mounted on a support pin 27 (44, 54, 64) of a support member 26 (43, 53, 61) on which the ultrasonic transducer 11 is fixedly mounted. A light emitting element 72 such as an LED and a light receiving element 73 such as a photodiode are disposed in opposing relationship on the opposite sides of the plate 71 to form the scan angle detection means. It is to be noted that a shaft on which the light shield plate 71 is mounted is not limited to the pins 27, 44, 54, 64, but may be any shaft which is connected with these pins through a suitable reduction gear.

When the scan angle detection means is constructed in this mannner, the light shield plate 71 moves as the transducer 11 rocks, thereby changing the amount of light incident on the light receiving element 73. In a corresponding mannner, the element 73 produces a varying photocurrent output, from which a scan angle of the transducer 11 can be derived. In the example shown, the light shield plate 71 has a rectilinear top edge 71a, but such edge may be shaped into a given curvilinear form so that the element 73 produces a photocurrent output proportional to sin $\theta$ or cos $\theta$ where $\theta$ represents a scan angle of the transducer 11. In this manner, a function generator circuit in an imaging apparatus to be described later can be simplified.

Figure 10:
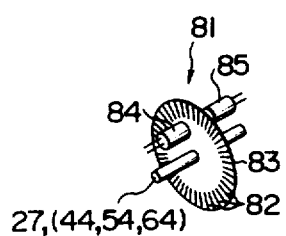

FIG. 10 shows another example of the scan angle detection means for the ultrasonic transducer in the form of a rotary encoder 81. The encoder 81 comprises a transparent disc 83 mounted on one of the pins 27, 44, 54, 64 and having a plurality of radially extending opaque lines inscribed along its periphery, and a light emitting element 84 and a light receiving element 85 aligned with each other and disposed on the opposite sides of the disc 83 at a peripheral position. In this arrangement, the element 85 produces a pulse signal proportional to an angle of rocking motion of the transducer 11, thus following a scan angle $\theta$ thereof to be derived from the pulse signal. The precision of detecting the scan angle $\theta$ can be improved by mounting the disc 83 on a shaft which is connected with one of the pins 27, 44, 54, 64 through a suitable transmission mechanism. A pulse signal from the element 85 which indicates the scan angle $\theta$ may be used to trigger a transmitter circuit which generates an ultrasonic pulse, thus allowing a tomographic image to be obtained which is of a sector scan form having a scanning line for each angular increment. In addition, the linear potentiometer 32 shown in FIG. 2 may be replaced by a linear encoder to constitute scan angle detection means.

Figure 11:
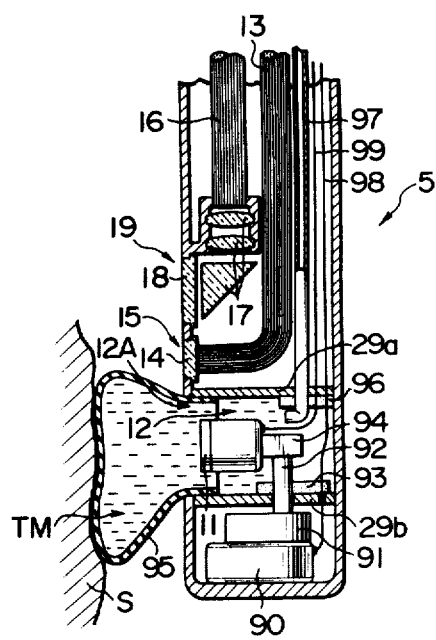
FIG. 11 is a longitudinal cross section of another form of the mechanical scanning assembly of the system shown in FIG. 2.

FIG. 11 shows an alternative form of drive means for the ultrasonic transducer 11. In the example illustrated, the drive means essentially comprises a miniature drive motor 90 housed within the foremost portion of the distal end 5, and a drive translating and transmitting mechanism 91 which translates a rotational motion of the output shaft of the drive motor 90 into a rocking motion with a speed reduction, for transmission to a rotatable shaft 92. The mechanism 91 may comprise a reduction gear. The shaft 92 extends into the housing 12 through a partition wall 29b which defines the housing 12 and a gasket 93 which prevents a water leakage. A support member 94 is integrally mounted on the free end of the shaft 92 and fixedly carries an ultrasonic transducer 11. When the drive motor 90 comprises a pulse motor which rotates through an angle of 60° per pulse, the mechanism 91 may be constructed to convert such angular increment into an angular movement of 12', thus with a reduction rate of 1/300.

In the ultrasonic diagnosis system described, the housing 12 has an opening 12A which is closed by an enclosure 95 formed of a highly resilient material such as a rubber diaphragm. A liquid supply and exhaust tube 97 extends from the proximate end operator 2 into the housing 12 by passing through a partition wall 29a and gasket 96. The liquid supply fills the housing 12 with an ultrasonic wave transmitting medium TM such as deaerated water. Consequently, the enclosure 95 is adapted to expand or shrink in accordance with the amount of medium TM supplied into the housing 12. In this manner, the enclosure 95 represents a reservoir for the ultrasonic wave transmitting medium TM, the purpose of which is to prevent absorption of ultrasonic energy by any gasous component present within a coeliac cavity and to transmit ultrasonic energy to tissues of a living body in an efficient manner. Hence, when an ultrasonic diagnosis is desired, the enclosure is caused to expand until it bears against the inner wall S of a coeliac cavity. When not in use, the enclosure is permitted to shrink, preventing any interference with the insertion of the endoscope into the coeliac cavity or an observation thereof. In FIG. 11, numeral 98 represents lead wires which transmit a drive signal to the drive motor 90, and 99 lead wires which transmit a signal to or from the ultrasonic transducer 11. While in the example shown, the enclosure 95 is formed of a highly resilient material such as rubber diaphragm, it should be understood that it may be constructed in a collapsible manner by forming it as a bellows mechanism which can be restored to a predetermined configuration.

FIG. 12 shows one form of means which may be used to supply and displace ultrasonic wave transmitting medium TM into or from the housing 12 which is closed by the enclosure 95. It comprises a combined feed and displacement pump 101, an operating unit 102 associated with the pump 101, a power supply 103, a reservoir 104 which stores a quantity of ultrasonic wave transmitting medium TM, and a supply and exhaust tube 105 which communicates with the supply and exhaust tube 97 through a connection pipe 108. The operating unit 102 may be activated to feed a drive current to the pump 101 from the power supply 103, and the pump then operates to supply medium TM from reservoir 104 into the housing 12 or conversely displace medium TM from the housing 12 to the reservoir 104.

A flowmeter or a pressure gauge may be disposed in a passage which is used to supply the medium TM to the inside of the enclosure 95 in order to monitor the amount of medium TM supplied to the housing 12 or to prevent a rupture of the enclosure 95. The operating unit 102 associated with the pump 101 may be mounted on the proximate end operator 2 of the endoscope 1, or may comprise a foot-operated switch so as to be operated by foot. Instead of using the combined feed and displacement pump 101, a feed pump and a suction pump may be separately provided to effect the supply and displacement of the medium TM to or from the enclosure 95 through two independent lines.

Figure 13:
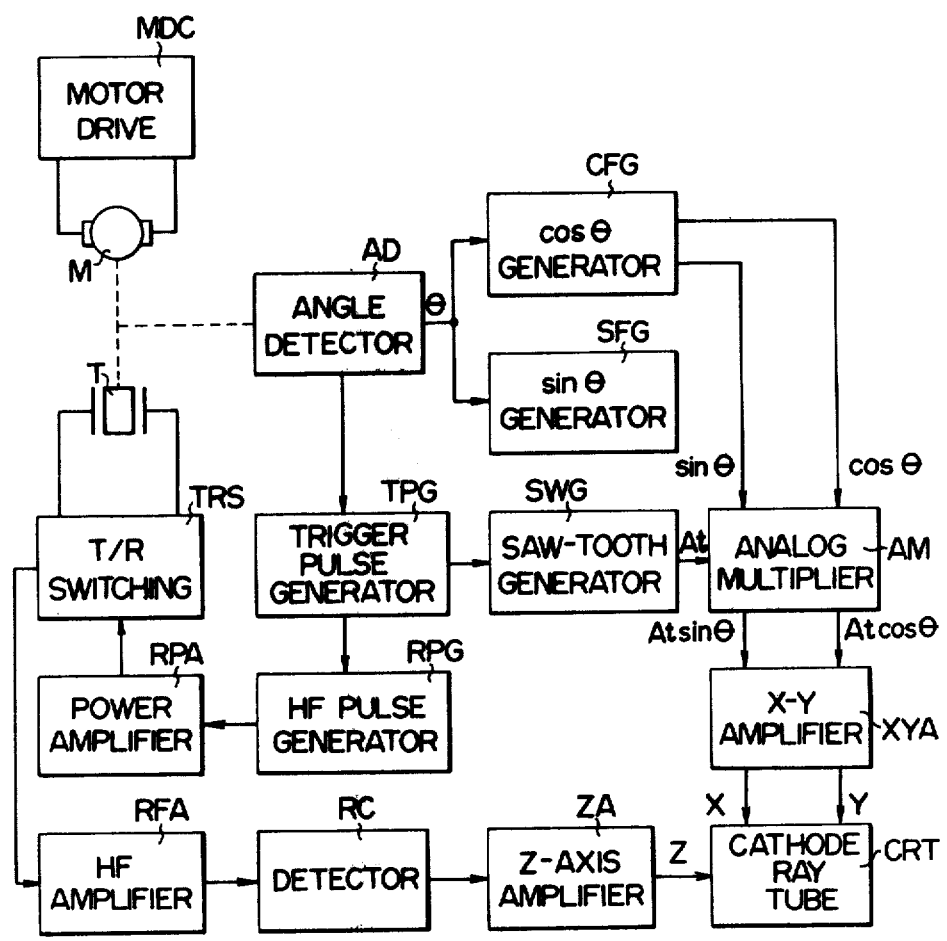
FIG. 13 is a block diagram of an electrical circuit of an imaging apparatus used in the system of the invention.

FIG. 13 shows one form of an imaging apparatus included in the ultrasonic diagnosis system of the invention. The imaging apparatus comprises a drive motor M which constitutes drive means for a transducer T which is formed by the ultrasonic transducer 11, a drive circuit MDC associated with the motor M, a scan angle transducer means or detector AD for the transducer T, a sine function generator SFG and a cosine function generator CFG which produce a sine and cosine function value of a scan angle $\theta$ in response to an output from the scan angle detector AD, a trigger pulse generator TPG responsive to an output from the detector AD for producing a trigger pulse at a given value of the scan angle $\theta$ which corresponds to one of scanninng lines, a high frequency pulse generator RPG for producing a drive signal which excites the transducer T for oscillation in response to a trigger pulse from the generator TPG, a power amplifier RPA for amplifying an oscillation drive signal from the pulse generator RPG, a transmit/-receive switching circuit TRS which connects the amplifier RPA to the transducer T for oscillation in the presence of an output from the power amplifier RPA and which feeds an output from the transducer T, produced in response to an echo received thereby, to a brightness modulator in the absence of an output from the power amplifier RPA, a saw-tooth wave generator SWG responsive to a trigger pulse from the trigger pulse generator TPG to produce a saw-tooth wave At (where A represents a constant, and t represents time beginning with the initiation of the trigger pulse input), an analog multiplier AM which multiplies the saw-tooth wave At by deflection signals sin $\theta$ and cos $\theta$ produced by the sine and the cosine function generator SFG and CFG, respectively, X- and Y-axis amplifier XYA which amplifies output signals At sin $\theta$ and At cos $\theta$ from the analog multiplier AM, a high frequency amplifier RFA which forms an input stage of the brightness modulator described above and which amplifies the echo output from the transducer T, a detector RC which extracts a signal of the oscillation frequency f of the transducer T from the output of the high frequency amplifier RFA, a Z-axis amplifier ZA which amplifies a detected output from the detector RC and feeds it as a brightness modulation signal, and a cathode ray tube CRT which reconstruct an ultrasonic tomographic image based on the scan signals from the X- and Y-axis amplifiers XYA and the brightness modulation signal from the Z-axis amplifier ZA and displays it as a visual image.

It is to be noted that the drive motor M and the transducer T disposed in the distal end 5 of the endoscope 1 are connected to the imaging apparatus provided externally of the endoscope through the connection pipe mentioned above.

The operation of the ultrasonic diagnosis system of the invention will now be described in terms of the imaging apparatus shown in FIG. 13 combined with arrangement shown in FIGS. 11 and 12.

Initially, the endoscope 1 shown in FIG. 12 is inserted into a coeliac cavity with the distal end 5 first. When the distal end 5 reaches a desired location within the cavity, the operating unit 102 is operated to supply the ultrasonic wave transmitting medium TM into the housing 12 shown in FIG. 11 to cause the enclosure 95 to expand. Subsequently, the enclosure 95 is brought into abutment against a desired area on the inner wall S of the coeliac cavity. The motor drive circuit MDC shown in FIG. 13 is then turned on to feed the drive motor M with the drive current, thus operating it. Thereupon, the rotational motion of the output shaft of the motor M is transmitted to the translating and transmitting mechanism 91, which translates such motion into a rocking motion, with a speed reduction, which is transmitted to the support member 94 mounted on the support shaft 92. In response thereto, the ultrasonic transducer 11 rocks about the axis of the shaft 92 in the radial plane of the distal end 5 to initiate a scanning of tissues within the physical body. The angle within the ultrasonic transducer 11 or the transducer T of FIG. 13 assumes during its rocking motion is detected as a scan angle $\theta$ by the scan angle detector AD and fed to the sine function generator SFG and the cosine function generator CFG. At the same time, at selected values of the scan angle $\theta$ which correspond to the individual scanning lines, the scan angle detector AD produces a signal which is fed to the trigger pulse generator TPG to cause it to produce a trigger pulse. The trigger pulse is fed to the high frequency pulse generator RPG and the saw-tooth wave generator SWG. In response thereto, the high frequency pulse generator RPG generates an oscillation drive signal for the transducer T at the oscillation frequency f thereof for a duration $\tau$. The oscillation frequency f is chosen to be on the order of 1 to 10 MHz. In particular, with the present ultrasonic diagnosis system, since the ultrasonic transducer 11 is inserted into the coeliac cavity together with the endoscope to permit an imaging of internal tissues from a relatively close location, the absorption of ultrasonic energy by these tissues is reduced, permitting a high frequency on the order of 5 to 10 MHz to be used, thereby improving the resolution of the image. The duration of electrical oscillation is chosen to be on the order of 1 μS so as to be sufficiently less than the time interval required for the ultrasonic wave to be reflected by internal tissues as a result of an impedance mismatch and to return to the transducer T.

The oscillation drive signal produced by the high frequency pulse generator RPG is amplified by the power amplifier RPA before it is applied to the transducer T through the transmit/receive switching circuit TRS. As a result, the transducer T is caused to oscillate at the frequency f and for the duration $\tau$, emitting ultrasonic pulse toward the interior of a living body through the ultrasonic wave transmitting medium TM shown in FIG. 11.

The ultrasonic pulse emitted toward the interior of the living body impinges on various tissues which have an acoustical impedance $Z = \rho C$ (where $\rho$ represents the density of a tissue and C a velocity of sound within the tissue). As a result of the impedance mismatch, the pulse is reflected at a boundary of tissues and returns to the transducer T, causing it to resonate to produce an echo signal across the electrode layers. It will be appreciated that several boundaries may be present between adjacent tissues as one proceeds in one direction of transducer T, so that the ultrasonic pulse is reflected from each boundary, and a time sequence of echo pulses are produced by the transducer T in a manner corresponding to the distance to the respective boundaries. These pulses are supplied to the high frequency amplifier RFA through the transmit/receive switching circuit TRS. The detector RC extracts a signal of the same frequency as the oscillation frequency f of the transducer T after the signal is amplified by the amplifier RFA, and supplies the extracted signal to the Z-axis amplifier ZA. After being amplified by the Z-axis amplifier ZA, the signal is applied to the cathode ray tube CRT as a brightness modulation signal Z.

On the other hand, in response to the trigger pulse from the generator G, the saw-tooth wave generator SWG produces a saw-tooth wave At beginning in time coincidence with the trigger pulse. The saw-tooth wave At is multipled by a sine value $\sin \theta$ and a cosine value $\cos \theta$ of the scan angle $\theta$, which are produced by the respective function generators FSG and CFG, in the analog multiplier AM, and the resulting products are amplified in the X- and Y-axis amplifier XYA as horizontal and vertical signals for input to the cathode ray tube CRT as signals X, Y which define scanning lines. Accordingly, a scanning line l is depicted with time on the screen of the cathode ray tube CRT as shown in FIG. 14. The line l intersect with a scanning line $l_O$ for the scan angle $\theta = 0$, shown in dotted lines, at an origin O and forms an angle of inclination of $\theta$ with respect thereto. However, it should be understood that the display formed on the screen of the tube CRT is not the scanning line l itself in the form of a single bright line, but is in the form of bright points $m_1$, $m_2$ which are located in time coincidence with the occurrence of the brightness modulation signal Z.

When a single scan along a single scanning line is completed in this manner, the rotation of the drive motor M moves the transducer T to a position having a scan angle which corresponds to the next scanning line. By way of example, when the scanning lines are spaced apart at an interval of 12', the next position will correspond to a scan angle of $\theta + 12'$. A similar process is then repeated. As a result of such repeated scans, a locus representing the position of boundaries of tissues will be displayed on the screen of the cathode ray tube CRT in terms of bright lines, which represent a desired reconstructed image of tissues of the physical body in accordance with the polar coordinate system. Thus, an ultrasonic sector scan, tomographic image I of tissues of the physical body is formed in accordance with the ultrasonic diagnosis system of the invention.

FIG. 15 shows another form of imaging apparatus which includes, in addition to a motor $M_1$ disposed within the distal end 5 in order to drive the transducer T, another motor $M_2$ disposed in the proximate end operator 2 and operated in synchronized relationship with the motor $M_1$ in order to detect a scan angle. Obviously, the purpose of providing the second motor $M_2$ at the proximate end is to permit the scan angle detector AD to be disposed within the imaging apparatus rather than in the distal end 5. It will be appreciated that this arrangement is adopted here because of the difficulty of placing a scan angle detecting means within the distal end 5 inasmuch as the ultrasonic diagnosis system of the invention must be disposed in a very limited space of the distal end 5 of the endoscope, even though such difficulty will not be experienced with a conventional ultrasonic diagnosis system which emits ultrasonic beam from the outer surface of the physical body and hence is not subject to a limitation on its size or configuration. Specifically, the second motor $M_2$ which is used to detect the scan angle is connected to the scan angle detector AD. Because the motor $M_2$ is operated in synchronism with the drive motor $M_1$, a knowledge of an angular movement of the output shaft of the motor $M_2$ permits the scan angle $\theta$ of the transducer T to be indirectly detected. The both motors $M_1$ and $M_2$ are manufactured to the same specification, and are driven from a synchronized signal from the common motor drive circuit MDC.

It is to be understood that the feature of this embodiment resides in the fact that a knowledge about the movement of the ultrasonic transducer 11 disposed within the distal end 5 can be gained indirectly outside the latter, and it should be understood that a number of modifications and changes from this arrangement are possible. For example, when the drive motor $M_1$ (90) is associated with the drive translating and transmitting mechanism 91 as shown in FIG. 11, the scan angle detecting motor $M_2$ is similarly associated with a drive translating and transmitting mechanism. Since it is only necessary that the output shaft of the motor $M_2$ connected with a detecting rod of the scan angle detector AD be synchronized with a rocking motion of the ultrasonic transducer 11, it is not essential that the both motors $M_1$ and $M_2$ be manufactured to the same specification. Furthermore, by a suitable choice of the relationship between the motor $M_2$ and the scan angle detector AD, $\sin \theta$ and $\cos \theta$ outputs can be directly obtained from the detector AD without using the sine and the cosine function generator SFG and CFG.

Figure 16:
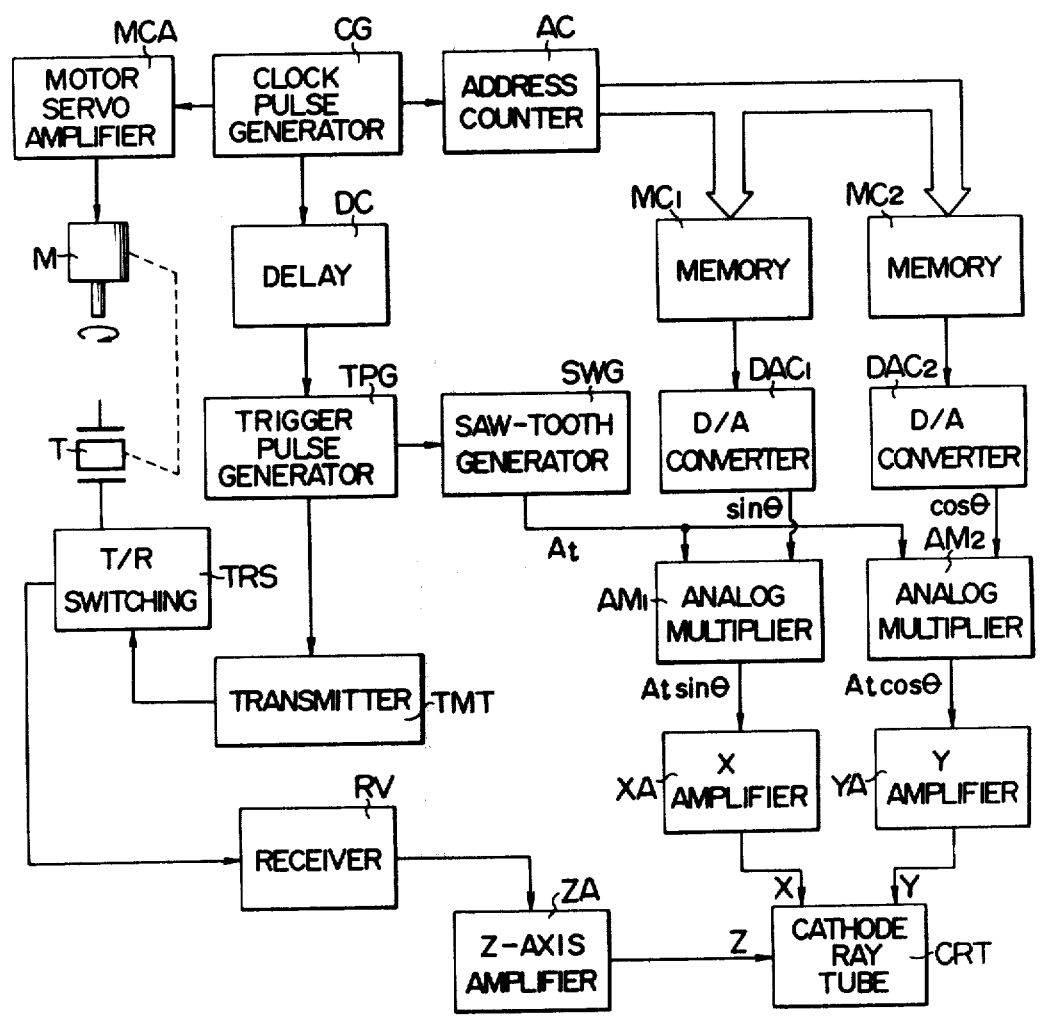

FIG. 16 shows a further form of imaging apparatus. The imaging apparatus shown includes a clock pulse generator CG which produces a clock pulse signal to operate the drive motor M. The clock pulse signal is also counted by an address counter AC which provides an address signal used to read out a sine and a cosine function value which are stored in memory circuits $MC_1$ and $MC_2$, respectively, thus deriving deflection signals. Specifically, a clock pulse signal from the generator CG is fed to a motor servo amplifier MCA, address counter AC and delay circuit DC, respectively. The motor servo amplifier MCA responds to the clock signal by rotating the drive motor at a constant rate. Hence, the transducer T also undergoes a rocking motion at a uniform rate. The counter AC counts the clock pulse signal, and its count is fed to the memory circuits $MC_1$ and $MC_2$ as an address signal. The both memory circuits $MC_1$, $MC_2$ are formed by Read Only Memories (ROM), and store sine and cosine function values (sin $\theta$, cos $\theta$) of a scan angle $\theta$ which is represented by the address signal. These function values sin $\theta$, cos $\theta$ are read therefrom in response to the address signal. These function values as read are in the form of digital values, which are then converted into corresponding analog values by D/A converters $DAC_1$, $DAC_2$ and fed to one input of each of analog multipliers $AM_1$, $AM_2$. The clock pulse signal applied to the delay circuit DC is delayed by a given time interval which compensates for a time lag in the operation of the drive motor M before it is fed to the trigger pulse generator TPG. In response to the delayed clock pulse signal, the generator TPG generates a trigger pulse, which is applied to a transmitter TMT comprising a high frequency pulse generator and a power amplifier, and also applied to a saw-tooth wave generator SWG. The transmitter TMT produces an oscillation drive signal which is supplied to the transducer T through a transmit/receive switching circuit TRS, thus exciting it for oscillation at an ultrasonic frequency. An echo reflected by the tissues of the physical body is received by the transducer T and is fed through the switching circuit TRS to a receiver RV which comprises a high frequency amplifier and a detector and which outputs a brightness modulation signal. On the other hand, in response to the trigger pulse, the saw-tooth wave generator SWG produces a saw-tooth wave At as a sweep signal, which saw-tooth wave is multiplied by deflection signals or function values sin $\theta$, cos $\theta$ in the analog multipliers $AM_1$, $AM_2$ to provide inputs to X-axis amplifier XA and Y-axis amplifier YA which in turn produce output signals X, Y defining a scanning line to be displayed.

When the imaging apparatus is constructed in this manner, a count of clock signals enables an angular position of the drive motor M or the scan angle $\theta$ of the transducer T to be known, eliminating the need for a separate provision of scan angle detection means. This enables the distal end 5 of the endoscope to be reduced in size and weight.

Figure 17:
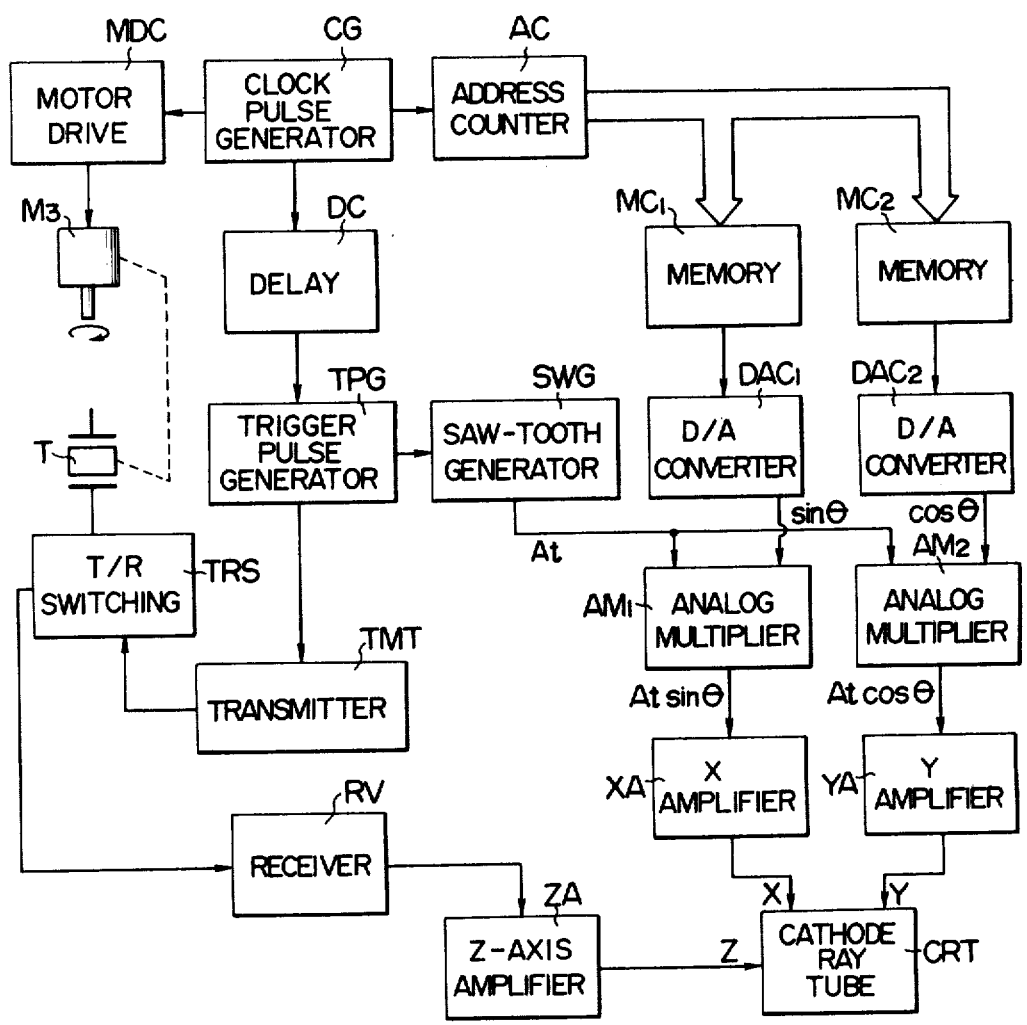

FIG. 17 shows still another form of imaging apparatus, which represents a modification of the imaging apparatus shown in FIG. 16 in that a usual d.c. motor which is used as the drive motor M is replaced by a pulse motor $M_3$. With this arrangement, the drive motor $M_3$ can be reversed by means of the motor drive circuit MDC which responds to a clock pulse signal from the clock pulse generator CG, so that it becomes unnecessary to employ the drive translating means 91 in order to translate the rotation of the drive motor $M_3$ into a rocking motion of the ultrasonic transducer 11, thus further simplifying the drive means associated with the ultrasonic transducer 11. Because the extent of rocking motion or scan of the ultrasonic transducer 11 is not determined mechanically, information which defines the extent of scan may be supplied to the motor drive circuit MDC and the address counter AC to select the extent of scan as desired. The selection takes place in a simple manner.

Figure 18:
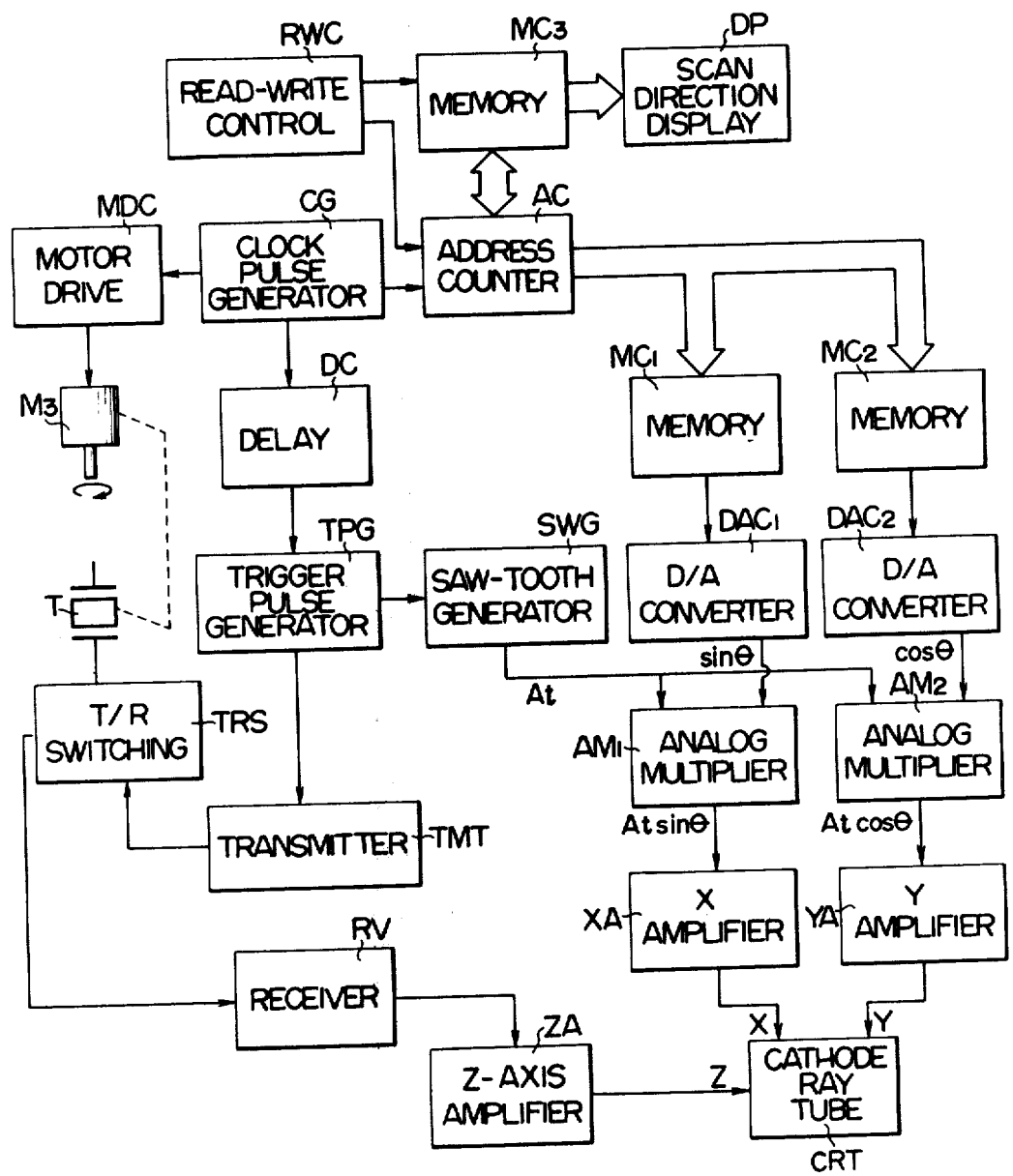

FIG. 18 shows an additional form of imaging apparatus which provides an external display of the direction in which the ultrasonic transducer is scanned. It will be seen from FIG. 18 that this imaging apparatus includes, in addition to the imaging apparatus shown in FIG. 17, a memory circuit $MC_3$ formed by a non-volatile memory such as magnetic or magnetic bubble memory and which stores a count contained in the address counter AC, a display unit DP which displays the stored content of the memory $MC_3$ as information indicative of the direction in which the ultrasonic transducer 11 is being scanned, and a read-write control circuit RWC which controls a flow of information between the memory $MC_3$ and the address counter AC.

With this arrangement, the direction in which the ultrasonic transducer 11 is being scanned is externally displayed by means of the display unit DP for the convenience of a user. In the event of a power failure in the process of scanning, the content of the address counter AC is retained in the memory $MC_3$, so that when the scanning operation is reinitiated, the stored content of the memory $MC_3$ can be read into the address counter EC by means of the control circuit RWC, allowing the scan to be continued from a position where it has been interrupted. Since the scan direction of ultrasonic transducer 11 can always be determined, the extent of scan can be established as desired, and a given area of the living body can be rescanned with good precision.

FIG. 19 shows a modification of the enclosure used in the ultrasonic diagnosis system of FIG. 11. The enclosure 111 shown is in the form of a pouch which surrounds and hermetically seals the ultrasonic transducer 11 and its support member 94. Part of the enclosure 111 is secured around the scan opening 12a, the free end of the liquid supply and exhaust tube 97 and support shaft 92, intermediate its length, in a water tight manner. This eliminates the need for the provision of partition walls which would define the housing for the ultrasonic transducer 11. A rupture or breakage of the enclosure 111 at the connection with the shaft 92 does not occur since the latter only oscillates, that is, only moves angularly through a limited extent.

The use of such enclosure dispenses with partition walls which would define the housing, allowing a further simplification of the ultrasonic diagnosis system.

FIG. 20 shows another form of mechanical scanning assembly of the ultrasonic diagnosis system of the invention. In the ultrasonic diagnosis systems shown in FIGS. 11 and 19, the miniature drive motor 90 is disposed adjacent to the ultrasonic transducer 11 housed within the distal end 5 of the endoscope 1 in order to cause a rocking motion of the transducer 11, thus achieving a mechanical sector scan of internal tissues. If a pulse motor having external dimensions on the order of 5 mm$\phi$ $\times$ 7 mm is used for the miniature drive motor 90, its maximum torque is on the order of 100 mg.cm. If a reduction gear head having a gear ratio of 200:1 and a transmission efficiency of 50% is used for the drive translating and transmitting mechanism 91, its output torque will be only 10 g.cm. On the other hand, the ultrasonic beam which is used for the purpose of diagnosis cannot be substantially transmitted through a gas, and hence the ultrasonic transducer 11 must be immersed in ultrasonic wave transmitting medium TM such as deaerated water, for example. When the transmitting medium TM is used, it is necessary to provide a liquid tight seal against such medium. The conventional seal for the liquid material such as the transmitting medium TM comprises a resilient member such as annular or sheet-shaped rubber material. If such seal is employed, there results a drawback of increased mechanical loss as a result of the friction occasioned by a direct contact of gasket member 93 (see FIG. 11) with shaft 92 which represents the output shaft of the drive motor 90 or the transmitting mechanism 91.

To accommodate for this drawback, the present embodiment is constructed so as to seal the transmitting medium TM within the housing 12 in a manner to minimize the mechanical loss. Specifically, referring to FIG. 21, a magnetic circuit is provided around the rocking shaft 92 so as to produce a magnetic flux which passes therethrough. A magnetic fluid 112 is magnetically retained within the magnetic circuit so as to function as a seal member. The magnetic circuit comprises an annular permanent magnet 113 which is axially magnetized, and a pair of annular yokes 114a, 114b formed of a magnetically soft material and disposed so as to hold the permanent magnet 113 sandwiched therebetween. The shaft 92 is preferably formed of a magnetically soft material. The permanent magnet 113 is preferably formed of a material having a high maximum energy product, for example, samarium cobalt magnet. A magnetic gap is defined between the internal periphery of the yokes 114a, 114b and the shaft 92, and is filled with the magnetic fluid 112. It will be noted that adjacent to their inner periphery, the yokes 114a, 114b are tapered in order to increase the flux density in the magnetic gap. The magnetic fluid 112 may comprise a dispersion of fine powder of magnetizable material such as iron oxide $Fe_3O_4$ having a size on the order of 100 Å in a solvent such as diester in a manner to prevent a condensation thereof. Such fluid is commercially available by the trade name ferrofluidic sold by Ferrofluidic Co., in the United States. It should be noted that where water is used as the ultrasonic wave transmitting medium TM, a solvent for the magnetic fluid 112 should be hydrophobic. The outer periphery of the yokes 114a, 114b is secured to the internal surface of a cylindrical liner which defines the distal end 5 in a water tight manner.

With this arrangement, the magnetic fluid 112 is magnetically retained in a magnetic gap defined between inner periphery of the yokes 114a, 114b and the shaft 92 so that the drive motor 90 and the drive translating and transmitting mechanism 91 can be effectively sealed from the ultrasonic wave transmitting medium TM which fills the housing 12. A direct contact of gasket 93 with the shaft 92 which occurs as when a usual rubber packing is used (as in FIG. 11) is avoided, and the only resistance to the rotation of the shaft 92 is that caused by the viscosity of the magnetic fluid 112. Thus, the mechanical loss of the output torque is reduced to a minimal value, allowing the drive to be transmitted to the ultrasonic transducer 11 in a positive manner. It will be appreciated that this affords a greater advantage when a miniature motor having a reduced output torque is used as the drive motor 90. In particular, when a pulse motor is used as the drive motor 90, an additional advantage is gained in that a malfunctioning as a result of an increased load torque can be prevented.

It will be noted that in the arrangement of FIG. 20, the shaft 92 is directly attached to the ultrasonic damper layer 25 of the ultrasonic transducer 11 without using an intermediate support member. The purpose of such arrangement is to locate the center of rocking motion of the transducer 11 as close to the ultrasonic energy emitting surface as possible so that the ultrasonic transducer 11 of a greater size can be disposed within the limited space in the distal end 5. Other elements or members not specifically referred to are similar to those used in the ultrasonic diagnosis system of FIG. 11, and are designated by corresponding reference characters.

FIG. 22 shows alternative form of sealing means which may be used in place of that shown in FIGS. 20 and 21. The sealing means shown comprise a pair of permanent magnets 115a, 115b disposed in opposing relationship to each other and vertically above and below the shaft 92 so as to define narrow gaps therewith. An annular partition member 116 is molded by a non-magnetic material such as plastics, around the permanent magnets 115a, 115b to fix them, leaving a space around the shaft 92, and a quantity of magnetic fluid 112 fills the gaps defined between the shaft 92 and the magnets 115a, 115b in the central region of the partition member 116. The both permanent magnets 115a, 115b are formed wth semicircular recesses centrally in their opposing edges, and these recesses constitute together a nearly circular opening through which the shaft 92 extends. It is to be understood that the permanent magnets 115a, 115b are disposed so that opposite poles are located opposite to each other to define strong magnetic field in the gaps which magnetically retains the magnetic fluid 112 therein.

With this sealing means, a sealing effect is achieved which is similar to that obtained by the arrangement of FIGS. 20 and 21. In addition, the yokes 114a, 114b can be dispensed with, permitting a reduction in the axial thickness of the sealing means.

Figure 23A:
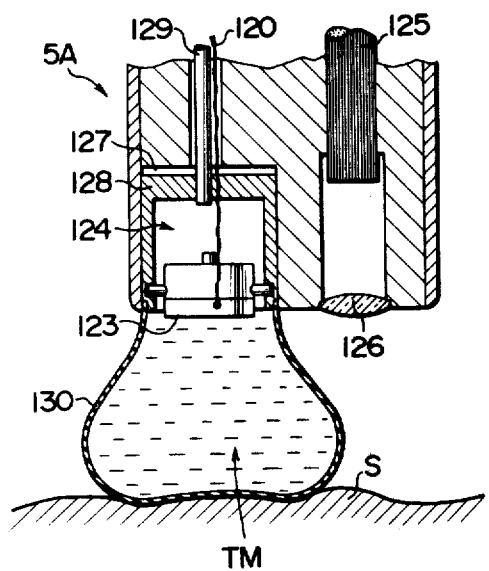
FIGS. 23(A) and (B) are cross sections of the mechanical scanning assembly of the ultrasonic diagnosis system according to another embodiment of the invention, FIG. 23(A) showing the system in use and FIG. 23(B) showing the system when not in use.
Figure 23B:
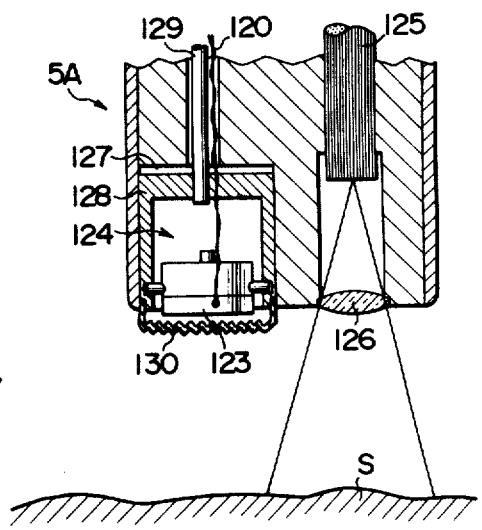

FIGS. 23(A) and (B) are cross sections showing a mechanical scanning assembly of an ultrasonic diagnosis system constructed according to another embodiment of the invention. An endoscope into which this diagnosis system is assembled is of a direct view type. Except for the construction of the distal end 5, it is constructed in generally the same manner as the endoscope of a lateral view type shown in FIG. 1. Hence, parts other than the distal end 5A will not be described.

Figure 24:
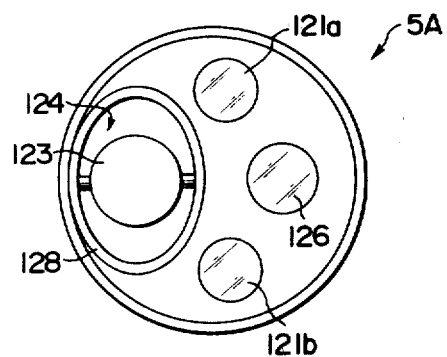
FIG. 24 is an end view of an endoscope in which the system shown in FIGS. 23(A) and (B) is disposed.

The endoscope of direct view type includes a distal end 5A, in the forward end face of which are formed illumination windows 121a, 121b, observation window 126 and a chamber 124 in which an ultrasonic transducer 123 is disposed, as shown in FIG. 24. The illumination windows 121a, 121b are formed by cover glasses which are disposed in opposing relationship with the end face of a bundle of optical fibres (not shown) forming a light guide from which the illuminating light is emitted. The observation window 126 defines by an objective optical system disposed in opposing relationship with the end face of a bundle of optical fibres 125 (see FIGS. 23(A) and (B)) forming an image guide and which also serves as a cover glass. The chamber 124 is defined by an elliptical housing 128 having a top which is fitted into and secured in a recess 127 formed in the distal end 5A. The housing 128 has a minor and a major axis, the lengths d and w of which must be chosen in a suitable manner depending on the outer diameter of the distal end 5A. By way of example, when the distal end 5A has an outer diameter of 14 mm, a choice can be made that $d=7$ mm, and $w=9$ mm. For an outer diameter of 12 mm of the distal end 5A, $d=6$ mm, and $w=9$ mm are a possible choice. The elliptical cross section of the housing 128 is merely an illustration to achieve a maximum utilization of the available space. Other configurations such as oblong housing cross section may also be utilized.

When this ultrasonic diagnosis system is inserted into a coeliac cavity, the ultrasonic wave transmitting medium TM is displaced out of the chamber 124 through the liquid supply and exhaust tube 129 to cause a shrinkage of the enclosure 130 in order to avoid an interference with the insertion. The insertion takes place while optically observing the interior of the coeliac cavity through the objective optical system and the image guide 125. When the distal end 5A of the endoscope is located opposite to a desired area of the coeliac cavity, the medium TM is supplied into the chamber 124 through the tube 129, as shown in FIG. 23(A), causing the enclosure 130 to expand until it bears against the inner wall S of the coeliac cavity. Subsequently, the ultrasonic transducer 123 is energized through lead wires 120 connected to a transmitter and receiver, and driven by drive means (not shown) for rocking motion.

Figure 25:
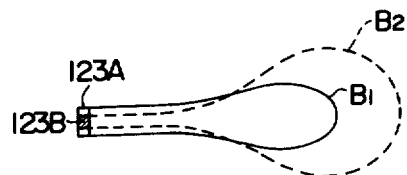
FIG. 25 is a schematic view illustrating the directivity lobe of the ultrasonic beam referenced to the diameter of the ultrasonic transducer.

The resolution of an ultrasonic diagnosis system involves a time resolution (resolution in the direction in which an ultrasonic beam progresses) and azimuthal resolution (a resolution in the direction perpendicular to the direction in which the beam progresses). Hence, in order to obtain an ultrasonic tomographic image of a high resolution, both of these resolutions must be improved. The time resolution is determined by the width of the ultrasonic pulse and the frequency thereof while the azimuthal resolution is determined by the directivity and geometrical configuration of the ultrasonic beam. Where the ultrasonic transducer 123 has a disc-shaped configuration, the directivity of the ultrasonic beam is determined by the frequency and the diameter of the disc. Thus, when the frequency is constant, the greater the diameter, the directivity is more sharp. Conversely, where the diameter is constant, the directivity increases its sharpness with an increase in the frequency. FIG. 25 schematically illustrates the lobe of the ultrasonic beam relative to the diameter of the transducer 123. Solid line $B_1$ represents a lobe for an increased diameter while broken lines $B_2$ represent a lobe for a reduced diameter. It will be appreciated that an absorption of the ultrasonic beam by the tissues of the living body will increase as the frequency is increased, making it difficult to perform an imaging from a depth within the living body. Consequently, there is a limit on the frequency which can be used in the ultrasonic diagnosis, so that it is desirable that the diameter of the ultrasonic transducer 123 be made as large as possible in order to improve the directivity (azimuthal resolution). However, in the ultrasonic diagnosis system of the invention, the transducer 123 must be assembled into the distal end 5A of the endoscope, so that the size of the transducer 123 which can be assembled is also limited. In addition, the ultrasonic transducer 123 must be rockably mounted and caused to rock rather, than simply assembling it into the distal end 5A. Consequently, it is very difficult to increase the diameter of the transducer 123.

Figure 26:
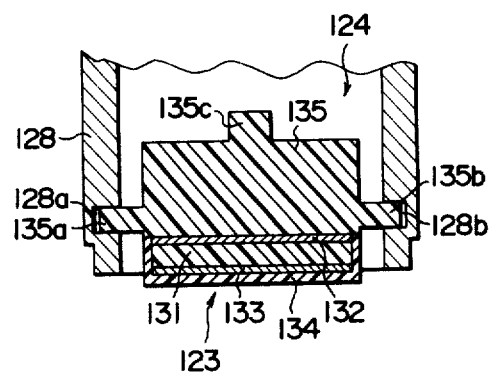
FIGS. 26 and 27 are cross sections of the ultrasonic transducer used in the system shown in FIGS. 23(A) and (B)

To cope with this problem, in the present embodiment of the ultrasonic diagnosis system, the radius of angular movement of the ultrasonic transducer 123, as defined by the spacing between the ultrasonic energy emitting surface and the axis of rocking motion, is reduced so that the transducer having an increased diameter can be used, as shown more fully in FIG. 26.

Specifically, the transducer 123 comprises a disc-shaped ultrasonic vibrator 131 with a pair of electrode layers 132, 133 applied to the upper and lower surfaces thereof. The lower surface of the electrode layer 133 which represents ultrasonic energy emitting surface and the lateral side of the transducer 123 are provided with an insulating cost 134. An ultrasonic damper layer 135 is secured to the upper surface of the electrode layer 132.

A pair of support pins 135a, 135b are formed integrally with the ultrasonic damper layer 135 and project from the opposite sides thereof in opposite directions. The pins 135a, 135b are fitted into a pair of bearing holes 128a, 128b formed in the housing 128 in a direction parallel to the minor axis thereof, whereby the transducer 123 is rockable about an axis including the pins 135a, 135b in a plane which includes the major axis of the housing 128. The upper surface of the ultrasonic damper layer 135 is formed with a driven projection 135c, to which a drive is imparted from means, not shown, for causing a rocking motion of the transducer 135.

Figure 27:
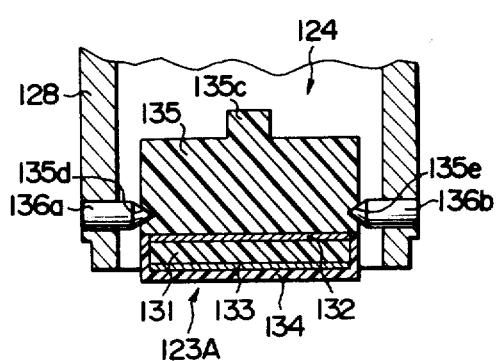

FIG. 27 shows another form of a mounting mechanism for the ultrasonic transducer. The ultrasonic transducer 123A is formed with a pair of conical bearing holes 135d, 135e in the opposite sides of its ultrasonic damper layer 135 in alignment with each other, and conical heads of pivots 136a, 136b which are embedded in the housing 128 fit in the holes 135d, 135e. In this manner, the transducer 123 is rockable about an axis defined by the holes 135d, 135e. It will be appreciated that the transducer 123A is operable in the same manner as the transducer 123 shown in FIG. 26.

Figure 28:
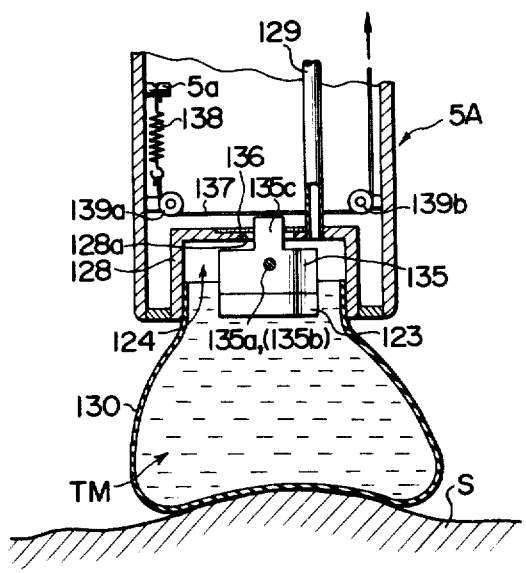
FIG. 28 is a cross section of one form of drive means which is used to drive the ultrasonic transducer shown in FIGS. 26 and 27.

FIG. 28 shows one form of drive means for the ultrasonic transducer 123. The driven projection 135c which is formed on the upper surface of the damper layer 135 extends through a loose opening 128a formed in the top wall of the housing 128 and into the distal end 5A. A water tight diaphragm 136 of a flexible material such as a rubber diaphragm is disposed around the projection 135c to maintain water tightness while permitting a movement of the projection 135c. Intermediate its length, a drive wire 137 is fixedly connected to the upper surface of the projection 135c. One end of the drive wire 137 is connected to a stationary member 5a on a cylindrical liner which defines the distal end 5A through a coiled tension return spring 138. The other end of the drive wire 137 extends to a drive unit (not shown) disposed in the proximate end operator 2. By pulling and releasing the drive wire 137, the transducer 123 can be rocked. In this Figure, reference characters 139a, 139b represent pulleys which are disposed at the bends of path of the drive wire 137.

Figure 29:
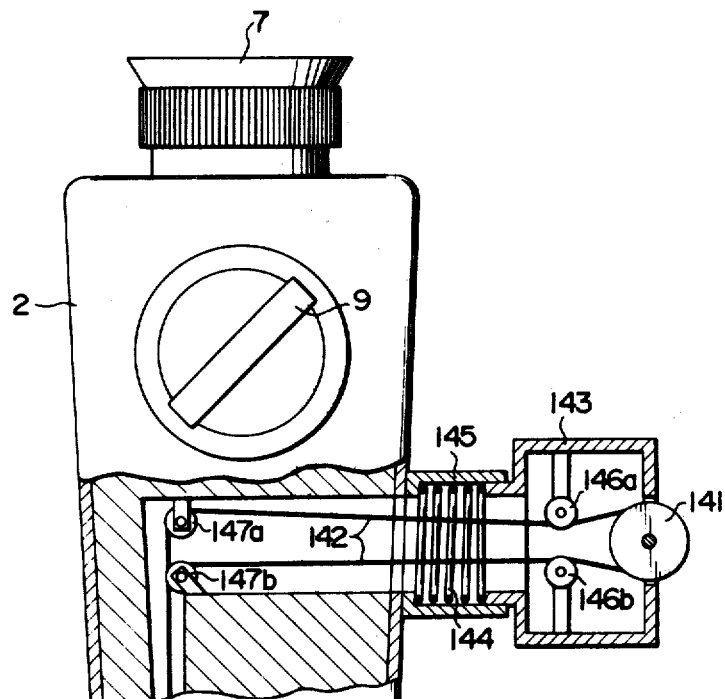
FIGS. 29, 30 are cross sections showing another form of drive means.
Figure 30:
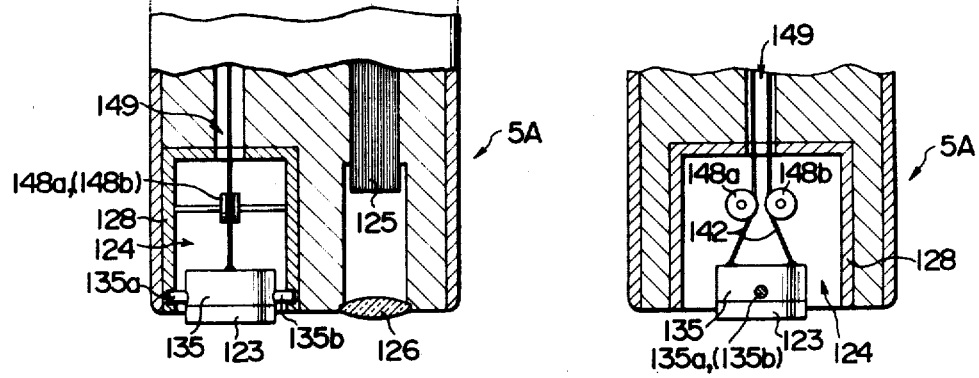

FIGS. 29 and 30 show another form of drive means for the ultrasonic transducer 123. In the present embodiment, the drive means comprises a drive pulley 141 connected to a drive unit (not shown) which may comprise a motor or the like, a drive wire 142 disposed on the pulley 141 and having its opposite ends anchored to the transducer 123, a holding frame 143 which rotatably supports the drive pulley 141, a coiled compression spring 144 urging the frame 143 to move in a direction to maintain the drive wire 142 taut, a housing frame 145 fixedly mounted on the proximate end operator 2 of the endoscope and housing the coiled spring 144, and three pairs of pulleys 146a, 146b, 147a, 147b, 148a, 148b which are disposed to determine the path of the drive wire 142.

The drive wire 142 is constructed of a flexible wire material having a small elongation such as a piano wire. The intermediate length of the drive wire 142 is fixedly disposed on the drive pulley 141 while its opposite ends extend through a guide slot 149 which extends from the proximate end operator 2 to the distal end 5A of the endoscope to reach the distal end 5A where the wire is fixedly connected to the upper surface of the ultrasonic damper layer 135 associated with the transducer 123.

The locations where the opposite ends of the wire 142 are anchored to the damper layer 135 are chosen such that they lie in a plane perpendicular to the pivots 135a, 135b on the damper layer 135 and are equi-distantly located from these pivots.

Figure 31:
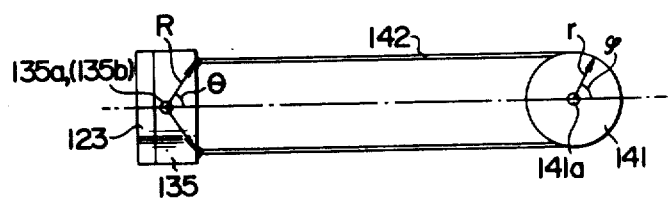
FIG. 31 is a schematic view illustrating the technique to detect a scan angle of the ultrasonic transducer shown in FIGS. 29 and 30.

When the drive means is constructed in this manner, the transducer 123 can be rocked through the drive wire 142 by rotating the drive pulley 141 by means of the drive unit. In this instance, as illustrated in FIG. 31, the transducer 123 will angularly move through an angle $\theta = r/R\phi$ where r represents the radius of the pulley 141, R the distance from the axis defined by the pivots 135a, 135b of the transducer 123 to the location of anchorage of the opposite ends of the drive wire 142 and $\phi$ the angle through which the pulley 141 is rotated from its central position. Thus, the scan angle $\theta$ of the transducer 123 is proportional to the angle of oscillation $\phi$ of the drive pulley 141, with r/R the constant of proportionality. Hence, by mounting an oscillating angle detecting means such as potentiometer on the shaft 141a of the pulley 141, the scan angle $\theta$ of the transducer 123 can be detected.

Figure 32:
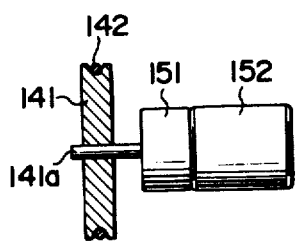
FIGS. 32 and 33 are cross sections of a drive mechanism which is used to drive a pulley shown in FIGS. 29 and 30.
Figure 33:
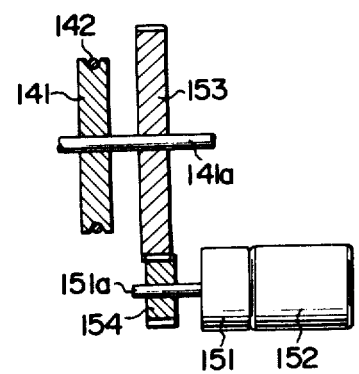

The drive unit which is connected to the drive pulley 141 may be constructed as shown schematically in FIG. 32. Specifically, the drive pulley 141 is directly connected with a rotatable shaft 141a which represents the output shaft of pulse motor 152 provided with a clutch and reduction gearing 151 which constitutes the drive translating and transmitting means. Alternatively, the drive pulley 141 may be mounted on a rotatable shaft 141a on which an intermediate gear 153 is fixedly mounted for meshing engagement with another intermediate gear 154 which is in turn fixedly mounted on the output shaft 151a of a pulse motor 152 having a clutch and reduction gearing 151, as shown in FIG. 33. Where a pulse motor 152 is used as drive means, drive pulses supplied to the motor 152 may be counted to derive a signal indicative of the scan angle $\theta$ of the transducer 123, thus enabling a separate scan angle detection means to be dispensed with.

FIG. 34 shows a further form of the drive means for the ultrasonic transducer 123. In the present example, drive means is constructed so that the ultrasonic transducer 123 automatically returns to a start position of the sector scan. Specifically, the drive means comprises a drive pulley 161 connected to a drive unit (not shown) which may comprise a motor, a drive wire 162 having its one end anchored to the pulley 161 and its other end secured to the transducer 123, a frame 163 which rotatably supports the drive pulley 161, a coiled compression spring 164 for urging the frame 163 in a direction to maintain the drive wire 162 taut, a housing frame 165 which houses the coiled spring 164, a pulley 166 used to change the direction of path of the drive wire 162, a conductive piece 167 applied to the upper surface of the damper layer 135, a conductive coiled tension spring 168 disposed between the conductive piece 167 and the housing 128, and a stop member 169 for the transducer 123 which is fixedly mounted on the housing 128 and which also serves as an electrode. The conductive spring 168 and the stop member 169 are connected to a display unit 171 through lead wires 170a, 170b.

With this arrangement, the display unit 171 enables an engagement of the stop member 169 with the conductive piece 167 to be recognized, so that a corresponding position of the transducer 123 may be chosen as a reference position or the start position for the sector scan. The drive pulley 161 is angularly driven against the resilience of the coiled spring 168 from this position, causing a scan operation of the transducer 123.

Again, a rotary potentiometer or a potentiometer which is designed to produce sin $\theta$ and cos $\theta$ functions may be connected to the rotatable shaft 161a of the drive pulley 161 as an angle detecting means, thereby enabling a scan angle $\theta$ of the transducer 123 to be derived.

FIG. 35 shows a modification of the mechanical scanning assembly shown in FIGS. 29 and 30 in that the assembly is associated with an enclosure. In this instance, the guide slot 149 through which the drive wire 142 extends passes between the chamber 124 which houses the transducer 123 and the proximate end operator 2 of the endoscope, so that when an enclosure 172 which closes the chamber 124 is provided, there must also be provided a liquid supply and exhaust tube 129 which supplies an ultrasonic wave transmitting medium TM to or displaces it from the chamber 124. In addition, the guide slot 149 must be isolated from the chamber 124 in a water tight manner. In the present instance, the guide slot 149 is isolated from the chamber 124 by providing a pipe-shaped water-tight diaphragm 173 which has its one end applied to the opening of the guide slot 149 and its other end disposed over the damper layer 135 in a manner to avoid interference with the pulling or releasing operation of the drive wire 142, and a conical coiled spring 174 disposed inside the diaphragm 173 so as to maintain it in a given configuration.

With this arrangement, the drive wire 142 is passed through the guide slot 149 by extending inside the spring 174, enabling an operation of the transducer 123 and isolating the guide slot 149 from the chamber 124 in a water tight manner.

Figure 36:
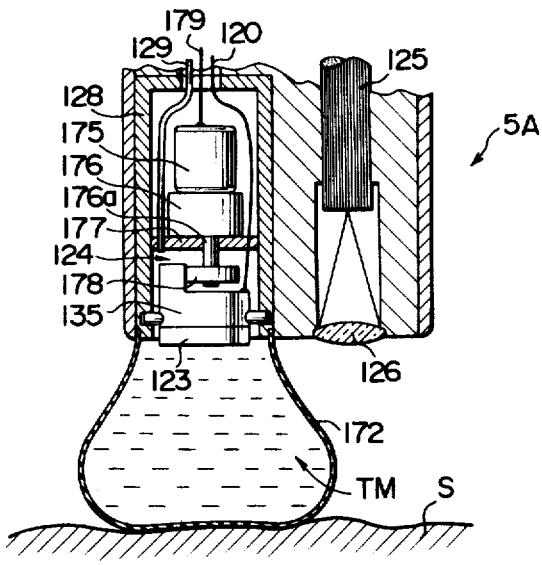
FIG. 36 is a cross section showing a still further form of the mechanical scanning assembly of the system of the invention.
Figure 37:
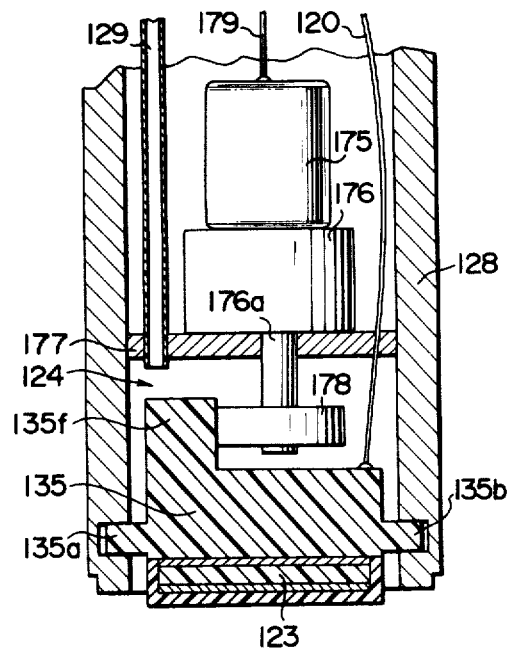
FIG. 37 is an enlarged cross section showing the detail of drive means for the ultrasonic transducer of the system shown in FIG. 36.

FIG. 36 shows an alternative form of mechanical scanning assembly which may be used in ultrasonic diagnosis system of the invention. In the present system, an ultrasonic transducer 123 is disposed in a distal end 5A of an endoscope of a direct view type and is adapted to be driven by a miniature driver motor 175 which is also disposed within the distal end 5A. As shown more fully in FIG. 37, the drive motor 157 is disposed within the upper portion of the housing 128 together with a reduction gearing 176 which represents a drive translating and transmitting mechanism. The reduction gearing 176 includes an output shaft 176a which extends through a partition wall 177 in a water tight manner and into the housing 124. A friction disc 178 is fixedly mounted on the free end of the output shaft 176a, and has its peripheral surface disposed in abutment against the lateral side of a projection 135f which projects from the upper end face of the ultrasonic damper layer 135 at its left-hand end. Thus, when the drive motor 175 is energized, the friction disc 178 is rotated through the reduction gearing 176 to cause a rocking motion of the transducer 123 which is disposed in abutment therewith. In this Figure, numeral 129 represents power feed lines to the drive motor 175.

Figure 38:
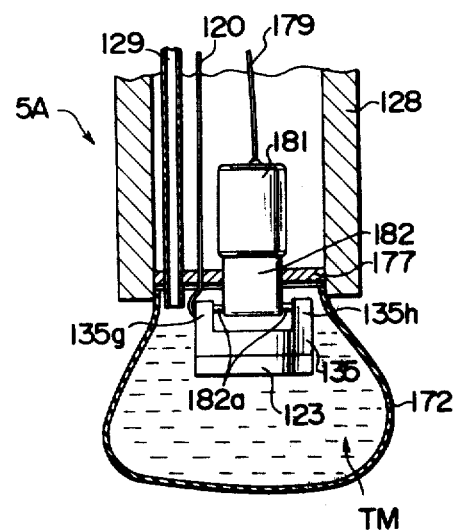
FIGS. 38 and 39 are cross sections showing alternative forms of drive means for the ultrasonic transducer shown in FIG. 37.
Figure 39:
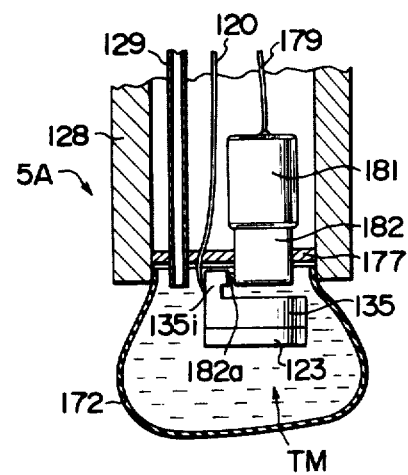

FIGS. 38 and 39 show an additional form of mechanical scanning assembly which may be used in the ultrasonic diagnosis system of the invention. In the present system, the ultrasonic transducer 123 is rocked for scanning purpose by means of a miniature drive motor 181 disposed within the distal end 5A, in the same manner as the system shown in FIGS. 36 and 37. Specifically, the drive motor 181 is associated with a reduction gearing 182 which represents a drive translating and transmitting mechanism. The reduction gearing 182 has an output shaft 182a which extends to one side or to both sides thereof. The upper portion of the ultrasonic damper layer 135 is integrally formed with a pair of supports 135g, 135h or a single support 135i which supports the output shaft 182a. Thus, the motor 181 may be operated to cause a rocking motion of the transducer 123 through a reduction gearing 182.

It will be understood that when the mechanical scanning assembly constructed as shown in FIGS. 36 to 39 is used in the ultrasonic diagnosis system, it operates in the same manner and achieves the same effect as that achieved by the use of the drive wire shown in FIGS. 29 to 34.

It should be understood that an imaging apparatus as shown in FIGS. 13 to 18 is directly applicable in those embodiments in which the ultrasonic diagnosis system is assembled into direct view type endoscopes as illustrated in FIGS. 23 to 39.

What is claimed is:

1. An ultrasonic diagnosis system located in an endoscope, said endoscope having a distal portion which is adapted to be inserted into a coeliac cavity and a proximate operating portion adapted to be located externally of said coeliac cavity, said system comprising:
a housing formed in the distal end of said portion of said endoscope, said housing having an opening therein;
an observation window and an illumination window of said endoscope located in the vicinity of said opening;
an ultrasonic wave transmitting and receiving transducer rockably disposed in said housing for transmitting and receiving ultrasonic waves through said opening;
drive means for causing a rocking motion of said ultrasonic transducer for the purpose of scanning internal tissues of a physical body;
scan angle transducer means disposed entirely in said distal portion of said endoscope for detecting the scan angle of said ultrasonic transducer and for generating an output responsive to said scan angle; and
an imaging apparatus for reconstructing a B-mode sector scan image of said internal tissues in response to an output transmitted by and an echo received by said ultrasonic transducer as well as said output of said scan angle transducer.

2. An ultrasonic diagnosis system according to claim 1 in which said endoscope is of a lateral view type and in which said housing is formed so that its opening opens into the periphery of the distal end of said portion of the endoscope and is directed in the same lateral direction as said observation and said illumination window.

3. An ultrasonic diagnosis system according to claim 1 in which said endoscope is of a direct view type and in which said housing is formed so that its opening opens into the front end face of the distal end of said portion of the endoscope and is directed in the same forward direction as said observation and said illumination window.

4. The ultrasonic diagnosis system according to claim 3 in which said endoscope extends from said proximate to said distal end generally along a first axis thereof and said ultrasonic transducer is rocked by the drive means for being rotated about a second axis, said second axis being substantially perpendicular to said first axis.

5. An ultrasonic diagnosis system according to claim 1 in which the housing is associated with an enclosure which extends through the opening thereof to cover the ultrasonic transducer to seal the housing in a water tight manner, and further including means for supplying an ultrasonic wave transmitting medium to or displacing it from the housing.

6. An ultrasonic diagnosis system according to claim 5 in which said enclosure is formed of a highly resilient material such as a rubber diaphragm.

7. An ultrasonic diagnosis system according to claim 5 in which said enclosure is of a collapsible type which can be restored to a predetermined configuration.

8. An ultrasonic diagnosis system according to claim 5 in which said enclosure is formed to surround the ultrasonic transducer in a water tight manner.

9. An ultrasonic diagnosis system according to claim 5 in which said means for supplying and displacing comprises a liquid supply and exhaust tube which has its one end opening into the housing, and wherein the endoscope includes a proximate end operator from which the ultrasonic wave transmitting medium can be supplied to or displaced from the housing through the tube.

10. An ultrasonic diagnosis system according to claim 5 in which said ultrasonic wave transmitting medium comprises deaerated water.

11. An ultrasonic diagnosis system according to claim 1 in which said ultrasonic transducer comprises an ultrasonic vibrator, a pair of electrode layers applied to the upper and the lower surface of the vibrator, an insulating coat applied to the surface of one of the electrode layers, and an ultrasonic damper layer secured to the surface of the other electrode layer.

12. An ultrasonic diagnosis system according to claim 11 in which said ultrasonic vibrator is formed of an electrostrictive material such as lead zirconate titanate or lithium niobate.

13. An ultrasonic diagnosis system according to claim 11 in which said ultrasonic damper layer comprises an ultrasonic energy absorbing material comprising powder of epoxy tungsten or tungstenate in admixture with an organic resin material such as epoxy resin.

14. An ultrasonic diagnosis system according to claim 1 in which said ultrasonic transducer is integrally mounted on a support member which is fixedly mounted on a rotatable shaft so as to be capable of a rocking motion.

15. An ultrasonic diagnosis system according to claim 1 in which said ultrasonic transducer comprises an ultrasonic energy emitting surface from which ultrasonic energy is transmitted into said tissues, and an ultrasonic damper layer, said damper layer absorbing all of the ultrasonic energy from a side of said transducer opposite said surface, said damper layer including at least one pin which is integrally formed with and projects from said ultrasonic damper layer for rockably supporting the transducer.

16. An ultrasonic diagnosis system according to claim 1 in which said ultrasonic transducer is formed with at least one bearing hole formed in the ultrasonic damper layer which is utilized to support the transducer.

17. An ultrasonic diagnosis system according to claim 1 in which said ultrasonic transducer has a planar, ultrasonic energy emitting surface.

18. An ultrasonic diagnosis system according to claim 1 in which said ultrasonic transducer has a concave, ultrasonic energy emitting surface.

19. An ultrasonic diagnosis system according to claim 1 in which said ultrasonic transducer is associated with an acoustical lens which is formed in the ultrasonic energy emitting surface thereof for causing a convergence of ultrasonic beam.

20. An ultrasonic diagnosis system according to claim 19 in which said acoustical lens is formed of an organic resin material such as epoxy resin.

21. An ultrasonic diagnosis system according to claim 1 in which said drive means comprises a drive motor disposed in a proximate end operator of the endoscope, a drive translating and transmitting mechanism for translating the rotation of the drive motor into a given drive output with a speed reduction, and drive transmitting means for transmitting the drive output from the drive translating and transmitting mechanism to the ultrasonic transducer.

22. An ultrasonic diagnosis system according to claim 21 in which said drive translating and transmitting mechanism comprises a reduction gearing.

23. An ultrasonic diagnosis system according to claim 21 in which said drive transmitting means comprises a drive wire having its end anchored to a support member associated with said ultrasonic transducer and adapted to slide in the axial direction of the endoscope.

24. An ultrasonic diagnosis system according to claim 21 in which said drive transmitting means comprises a drive wire having its end connected to a support shaft on which a support member associated with said ultrasonic transducer is rotatably mounted, said drive wire being adapted to move around the shaft circumferentially thereof.

25. An ultrasonic diagnosis system according to claim 21 in which said drive transmitting means comprises a drive pulley connected to said drive translating and transmitting mechanism, and a drive wire disposed on the drive pulley and having its opposite ends anchored to said ultrasonic transducer.

26. An ultrasonic diagnosis system according to claim 21 in which said drive transmitting means comprises a drive pulley connected to said drive translating and transmitting mechanism, and a drive wire having its one end secured to the drive pulley and disposed thereon and having its other end connected to said ultrasonic transducer which is urged by resilient means to rock in one direction.

27. An ultrasonic diagnosis system according to claim 25 or 26 in which said drive pulley is biased in one direction by resilient means so that said drive wire is maintained taut with a substantially constant tension.

28. An ultrasonic diagnosis system according to claim 21 in which said drive transmitting means comprises a drive wire having its one end secured to a stationary member through resilient means and thereby urged in one direction, part of said drive wire being coupled to said ultrasonic transducer.

29. An ultrasonic diagnosis system according to claim 1 in which said drive means comprises a drive motor disposed in the distal end of the endoscope, a drive translating and transmitting mechanism for translating the rotation of said drive motor into a given drive output with a speed reduction, and drive transmitting means for transmitting a drive output from the drive translating and transmitting mechanism to said ultrasonic transducer.

30. An ultrasonic diagnosis system according to claim 29 in which said drive translating and transmitting mechanism comprises a reduction gearing.

31. An ultrasonic diagnosis system according to claim 29 in which said drive transmitting means comprises the output shaft of the drive translating and transmitting mechanism which also serves as a support shaft for said ultrasonic transducer.

32. An ultrasonic diagnosis system according to claim 29 in which said housing is filled with an ultrasonic wave transmitting medium and in which said drive translating and transmitting mechanism is sealed from the ultrasonic wave transmitting medium by a magnetic fluid which fills a magnetic circuit formed at the boundary between the drive translating and transmitting mechanism and the housing of the ultrasonic transducer to extend through or along the output shaft of the drive translating and transmitting mechanism.

33. An ultrasonic diagnosis system according to claim 29 in which said drive transmitting means comprises a friction disc mounted on the output shaft of the drive translating and transmitting mechanism, and a driven projection formed on said ultrasonic transducer and engaged by the disc.

34. An ultrasonic diagnosis system according to claim 1 in which said drive means comprises a voice coil actuator disposed in the distal end of the endoscope and having its output shaft connected to said ultrasonic transducer.

35. An ultrasonic diagnosis system according to claim 1 in which said drive means comprises a pair of electromagnets disposed within the distal end of the endoscope and disposed in opposing relationship with each other on the opposite sides of a support member which is formed of a magnetically soft material and which rockably supports said ultrasonic transducer.

36. An ultrasonic diagnosis system according to claim 1 in which said scan angle transducer detecting means comprises a linear potentiometer disposed having an access shaft which is linked with said ultrasonic transducer.

37. An ultrasonic diagnosis system according to claim 1 in which said scan angle transducer detecting means comprises a rotary potentiometer having a rotatable shaft which is ganged with a support shaft which causes a rocking motion of said ultrasonic transducer.

38. An ultrasonic diagnosis system according to claim 1 in which said scan angle transducer detecting means comprises a combination of a light emitting element and a light receiving element disposed in opposing relationship with each other on the opposite sides of a light shield which is ganged with said ultrasonic transducer.

39. An ultrasonic diagnosis system according to claim 1 in which said scan angle transducer means comprises a rotary encoder which is ganged with said ultrasonic transducer, said encoder producing a plurality of signal pulses for every scan of said transducer over a range of less than substantially ninety degrees.

40. An ultrasonic diagnosis system according to claim 1 in which said imaging apparatus comprises a sine and cosine function generator which respond to said output of said scan angle transducer means by generating corresponding sine and cosine values.

41. An ultrasonic diagnosis system according to claim 1 in which said scan angle transducer means is located adjacent to said ultrasonic transducer.

42. An ultrasonic diagnosis system according to claim 1 in which said scan angle transducer means is disposed in said housing.

* * * * *